(12) United States Patent
Komatsu et al.

(10) Patent No.: US 8,091,426 B2
(45) Date of Patent: Jan. 10, 2012

(54) ULTRASONIC WAVE MEASURING METHOD AND APPARATUS

(75) Inventors: Shinsuke Komatsu, Osaka (JP); Yoichiro Ueda, Osaka (JP)

(73) Assignee: Panasonic Corporation, Osaka (JP)

( * ) Notice: Subject to any disclaimer, the term of this patent is extended or adjusted under 35 U.S.C. 154(b) by 673 days.

(21) Appl. No.: 12/295,504

(22) PCT Filed: Mar. 26, 2008

(86) PCT No.: PCT/JP2008/000729
§ 371 (c)(1),
(2), (4) Date: Sep. 30, 2008

(87) PCT Pub. No.: WO2008/129832
PCT Pub. Date: Oct. 30, 2008

(65) Prior Publication Data
US 2010/0224000 A1    Sep. 9, 2010

(30) Foreign Application Priority Data

Mar. 29, 2007    (JP) .................................. 2007-087280

(51) Int. Cl.
*G01N 29/44*    (2006.01)
(52) U.S. Cl. .......................................................... 73/602
(58) Field of Classification Search .................... 73/1.82, 73/1.86, 602
See application file for complete search history.

(56) References Cited

U.S. PATENT DOCUMENTS

| 4,168,629 A | 9/1979 | Bulteel |
| 5,684,252 A | 11/1997 | Kessler et al. |
| 6,089,095 A | 7/2000 | Yang et al. |
| 2003/0033878 A1 | 2/2003 | Dubois et al. |

FOREIGN PATENT DOCUMENTS

| JP | 63-172960 | 7/1988 |
| JP | 63-241351 | 10/1988 |
| JP | 5-333007 | 12/1993 |
| JP | 6-148153 | 5/1994 |
| JP | 6-294779 | 10/1994 |
| JP | 7-280542 | 10/1995 |
| JP | 7-303640 | 11/1995 |
| JP | 10-90237 | 4/1998 |
| JP | 2000-140781 | 5/2000 |
| JP | 2001-13115 | 1/2001 |
| JP | 2001-272339 | 10/2001 |
| JP | 2006-78208 | 3/2006 |

OTHER PUBLICATIONS

Patent Cooperation Treaty (PCT) International Preliminary Report on Patentability issued Oct. 20, 2009 in International Application No. PCT/JP2008/000729.

*Primary Examiner* — Hezron E Williams
*Assistant Examiner* — Rose M Miller
(74) *Attorney, Agent, or Firm* — Wenderoth, Lind & Ponack, L.L.P.

(57) ABSTRACT

In a comparison between master data created from a waveform signal of an observed object of an acceptable article and a waveform signal obtained from a non-measured observed object, time phase difference generated in the observed object is corrected, and difference with the master data is detected. As a first stage, quality determination is performed on the non-measured observed object with a long interval master data using the created master data, and the time phase difference is corrected. Then, as a second stage, quality determination is performed with the short interval master data divided on a time axis and the similarly divided waveform signal of the observed object. The time phase difference generated between the observed objects (acceptable article and defective article) is thereby corrected, and quality determination of high accuracy can be performed from the comparison with the waveform signal of the acceptable article.

3 Claims, 30 Drawing Sheets

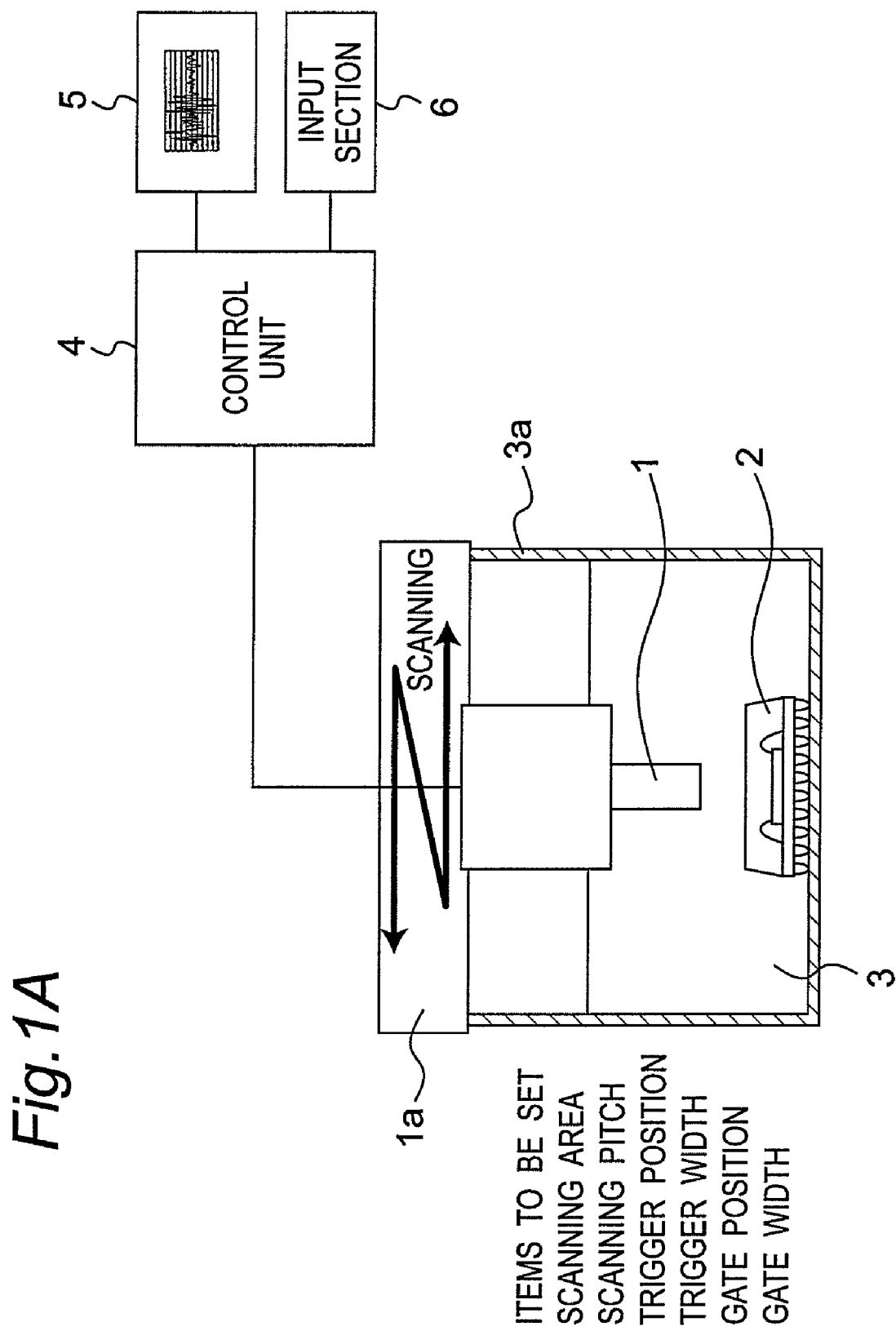

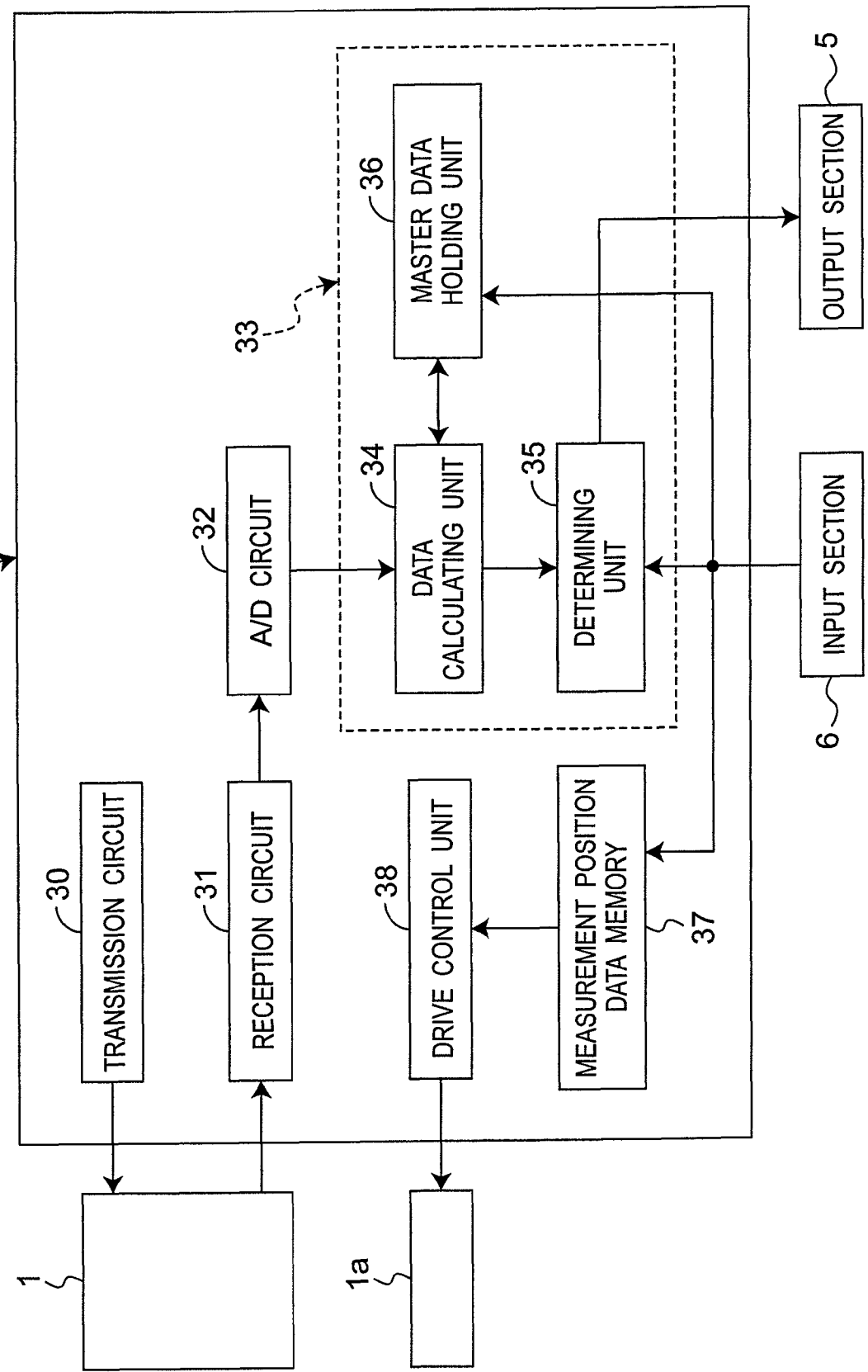

BGA CHIP
○ : OK ELECTRODE
● : NG ELECTRODE

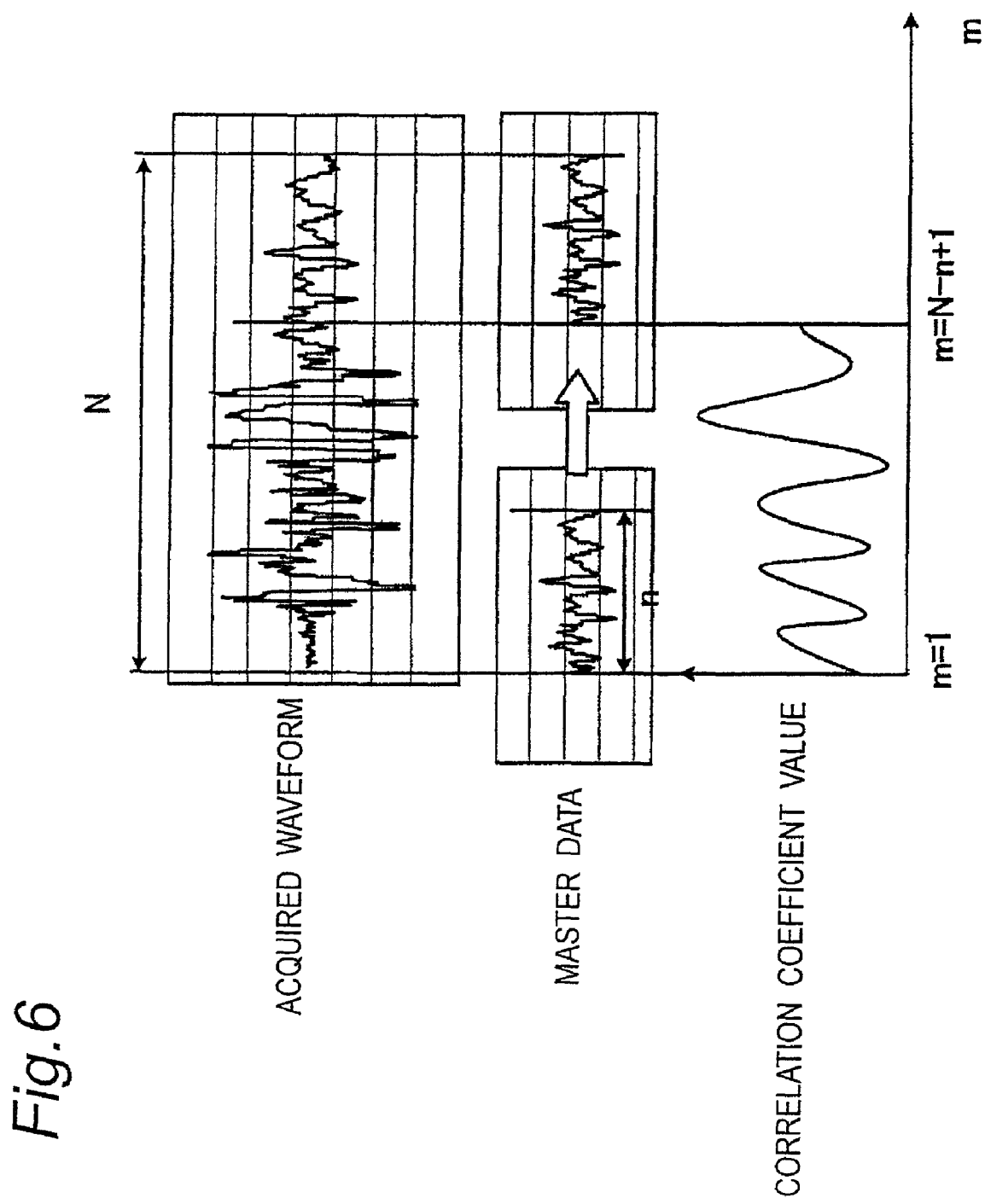

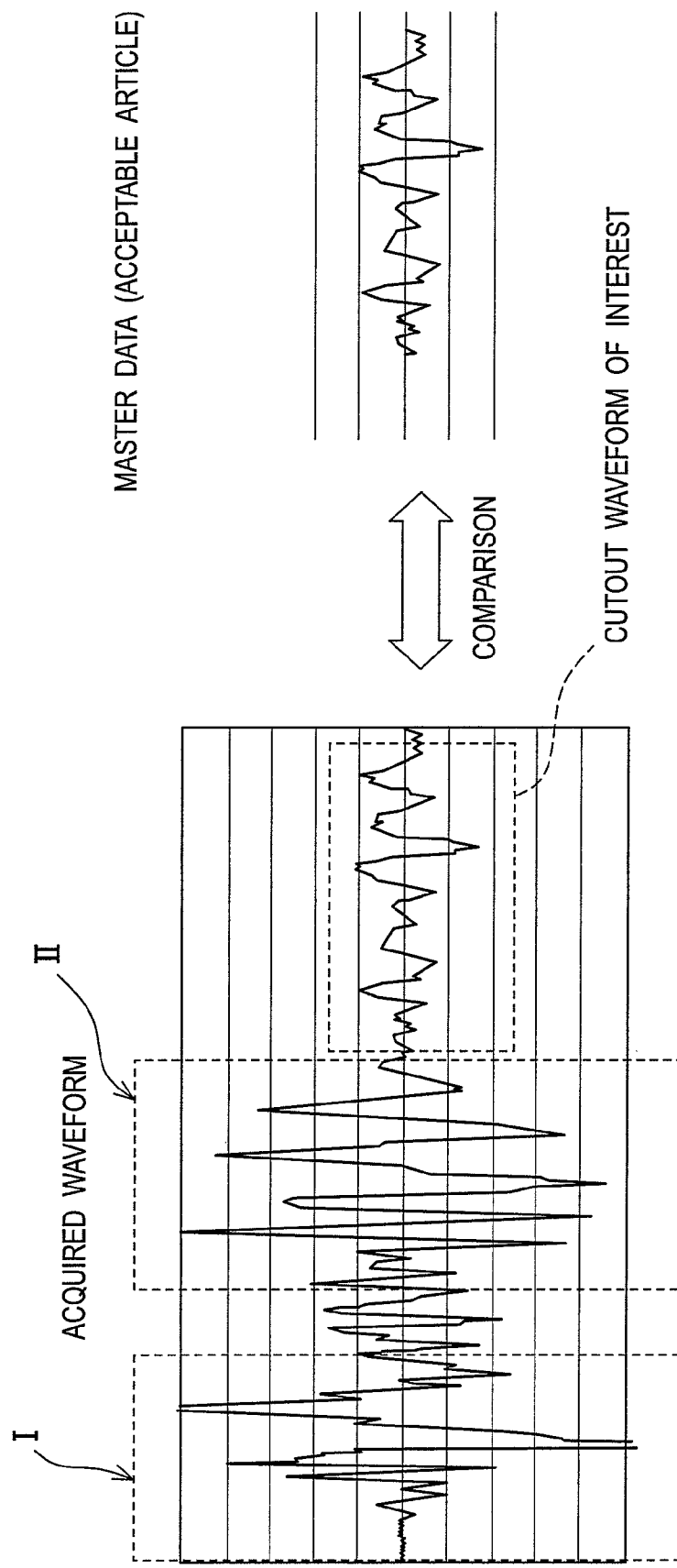

(MATCHING POINT IN LONG INTERVAL DETERMINATION)

(MATCHING POINT IN LONG INTERVAL DETERMINATION)

Fig.14
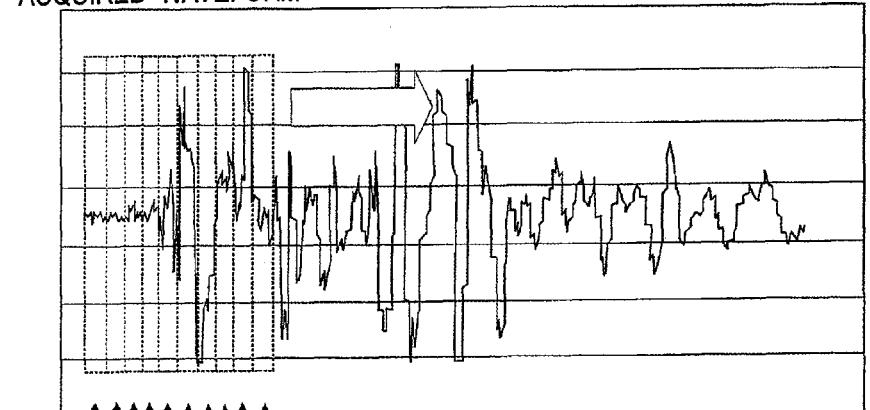
COMPARE EACH SHORT INTERVAL MASTER DATA
MOVE BY SET WIDTH
MASTER DATA (ACCEPTABLE ARTICLE)
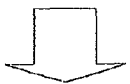
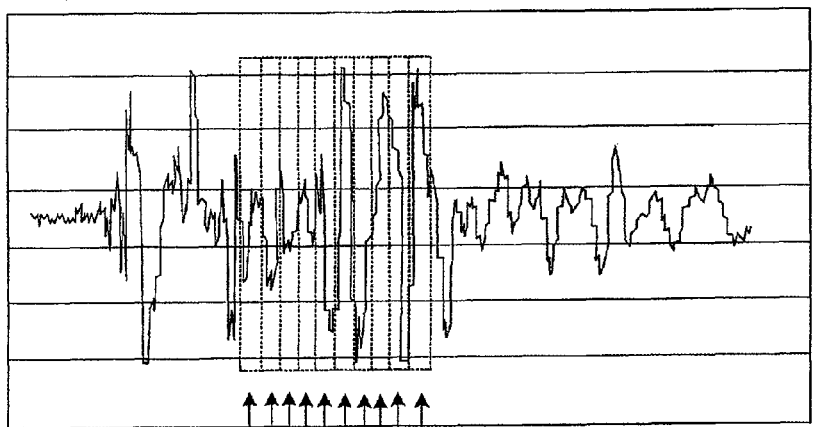
MASTER DATA (ACCEPTABLE ARTICLE)

PLAIN IMAGE

TIME WAVEFORM OF A-A' CROSS SECTION

DIFFERENCE IN ARRIVAL TIME EVEN AT SAME CROSS-SECTIONAL POSITION

ULTRASONIC WAVE MEASURING METHOD AND APPARATUS

TECHNICAL FIELD

The present invention relates to ultrasonic wave measuring method and apparatus capable of detecting and analyzing at high accuracy a defect such as joint separation or a crack of an observed object (object to be observed) having a microscopic thickness and interfaces of multi-layers.

BACKGROUND ART

FIG. 15 is a view showing a basic configuration of the most general ultrasonic wave measuring apparatus of the conventional art. The following description describes features in analyzing an ultrasonic reflected signal, but the basic method, aim, and solution are the same for systems using other means such as a transmission method.

As shown in FIG. 15, the ultrasonic wave measuring apparatus is configured by an ultrasonic probe 101, a control unit 104, and an input section 106, where an observed object (object to be observed) 102 is irradiated with an ultrasonic wave generated from the ultrasonic probe 101 with water 103 as a medium, the wave reflected from the observed object 102 is received by the ultrasonic probe 101, and waveform processing, image processing, and the like are performed in the control unit 104 based on information received by the ultrasonic probe 101 to determine quality of an interface and image the determination result. The ultrasonic probe 101 is used for both transmission and reception, and the control unit 104 includes a pulsar receiver for converting the ultrasonic wave received by the ultrasonic probe 101 to voltage and amplifying the same, and an image processing unit for imaging an intensity value of an observed waveform 105. An electronic package such as a semiconductor chip is assumed as a specific example of the observed object 102. The ultrasonic wave transmits even through the interior of the observed object 102, and the reflected wave generates even from the interior interface. Therefore, the signal received by the ultrasonic probe 101 has a waveform in which plural waves generated from plural interfaces are overlapping.

An example of the reflected waveform is shown in FIG. 16. Specific examples of the observed object serving as an object to be detected include an electronic package mounted on a board. An example for a case where the electronic package, which is a specific example of such an observed object, is submerged under water is shown in FIG. 17A. As shown in FIG. 17A, an electronic package 29, which is a specific example of the observed object, placed in liquid (water) 27 has a plurality of interfaces (e.g., respective contacting surfaces of a semiconductor chip 22, an interposer layer 23, a solder bump 24, a mother board 25, and the like), and thus a plurality of reflected waves 26 is reflected from the electronic package 29 when the electronic package 29 is irradiated with the ultrasonic wave. Such reflected waves 26 are outputted in a form where the plurality of reflected waves are combined, as shown in FIG. 16.

Another example of the detected object is shown in FIG. 18. In this example, an observed object 29A has a single structure, and does not have a plurality of boundary surfaces in the inner portion of the observed object as with the observed object 29 of FIG. 17A, where the reflected wave 26A of the ultrasonic wave is assumed to generate from two locations, the interface between water and the surface of the observed object 29A and the interface between a bottom surface of the observed object 29A and a bottom surface of a water tank. Thus, even if the observed object 29A does not have plural boundary surfaces, the reflecting interface of the ultrasonic wave always exists in plurals, and thus the reflected wave also exists in plurals, whereby a form in which the plurality of reflected waves are combined as in FIG. 16 is obtained.

An ultrasonic wave measuring method of making quality determination on the interface of the observed object with the ultrasonic wave measuring apparatus of the conventional art will be described with reference to FIG. 16. In the conventional art, a trigger 11 is first applied on a surface wave from which an ultrasonic waveform is stably generated. Then, the setting of a time region referred to as gate 12 is performed with the trigger 11 as a zero base point. The gate region needs to contain information of the interface to be observed. In other words, the reflected wave containing information on the interface to be measured is selected from the combined wave of the plurality of reflected waves generated due to the presence of a plurality of interfaces, and the gate 12 is set in the relevant time region. In addition to the gate position, the set value of the gate 12 includes gate width or number of gates.

The gate width is normally set to the reflected wave width of a time slot to be focused, and in most cases, set to a length of one cycle of a sinusoidal wave or shorter. The frequency band of the ultrasonic wave used in the electronic package is between about 10 and 100 MHz, and thus the gate width is often set between 10 and 100 ns. The number of gates is set in plurals to compare with other gate information when the information of the interface to be measured is unknown. Quality determination of the observed object 102 is performed mainly with the waveform intensity value within the interval of the gate 12 set in the above manner. The determination method includes determination using a maximum value and a minimum value (negative maximum value), the maximum value of the absolute value, or the like of the waveform intensity within the interval of the gate 12.

Patent document 1: Unexamined Japanese Patent Publication No. 5-333007

Patent document 2: Unexamined Japanese Patent Publication No 6-294779

DISCLOSURE SUMMARY OF INVENTION

Issues to be Solved by the Invention

However, information from the interfaces above the interface to be measured may have variation depending on the observed objects even though the observed objects are of the same type. Since the electronic package 29 has a plurality of interfaces as shown in FIG. 17A, phase difference actually occurs as shown in FIG. 19 even if trigger is matched with the surface of a resin mold 21 from which the reflected wave is stably generated, and the waveforms in different time intervals will be compared as a result even if the waveform is observed at the same gate position. The cause of phase difference includes variation in thickness of each layer, variation in sonic speed in the material, and the like. The material of the interposer layer 23 may be polyimide, ceramic, glass epoxy resin, or the like, but the time delay in ultrasonic wave transmission sometimes occurs in an XY plane due to the woven cloth structure of the glass fiber in the case of glass epoxy resin. FIG. 20A is a C-scope image (image observed from the upper surface side of a semiconductor chip 22) of the semiconductor chip 22 when the interposer layer 23 is made of glass epoxy resin. When cutting out the cross-sectional portion taken along line A-A' shown in FIG. 20A and observing the B-scope (plane-time scan image) of FIG. 20B, it can be found that there is difference in arrival time of the reflection echo even if the same time position is viewed in the reflected wave after the interposer layer 23.

Generally, the electronic package has a structure with a plurality of interfaces, and the thickness of each interface is thin (several tens to 500 μm), and thus a phenomenon in that the wave reflected from each interface superimposes occurs. In other words, as the sinusoidal ultrasonic wave generated from the probe becomes the reflected wave having temporal overlap in reception, the reflected wave containing the information of the interface to be measured does not become a sinusoidal wave but may be an addition thereof (include phase difference). The above issues are not conventionally found since the structure having a plurality of interfaces is rarely observed in the ultrasonic flaw detection and the thickness of the interface is large.

The frequency of the probe (greater than or equal to 100 MHz) is preferably raised to raise the time resolution, but as the high frequency ultrasonic wave is less likely to transmit in the depth direction, it may not be transmitted to the interface to be measured. Thus, waveform observation needs to be carried out at low frequency. The low frequency signal causes superimposing phenomenon described above. Since superimposition occurs in the waveform at the interface to be observed due to reasons described above when observing the electronic package, as shown in FIG. 21, it is sometimes difficult to make quality (good or bad) determination only by observing an amplitude value of the gate as in the conventional case. The difference in waveform is large in the region of the gate 12 of FIG. 21, but automatic determination cannot be made with the maximum value etc. of the amplitude value.

In view of solving the above issues of the conventional art, it is an object of the present invention to provide ultrasonic wave measuring method and apparatus capable of canceling the phase difference of the waveform containing information of the measuring interface of the observed object, and performing quality determination of the observed object other than with the amplitude value of the waveform.

Means for Solving the Issues

In order to achieve the above object, the present invention employs the following configuration.

In accomplishing the above objects, according to a first aspect of the present invention, there is provided an ultrasonic wave measuring method of irradiating with an ultrasonic wave an object to be detected having a plurality of interfaces, detecting a waveform signal generated from the object, and observing a joint state of a boundary face of the object, the ultrasonic wave measuring method comprising:

saving, for every observation spot of a reference object which cross-sectional structure, material, and thickness are the same as the object in a certain specific region within an XY plane orthogonal to a direction of irradiating with the ultrasonic wave, an entire waveform signal of the reference object or a waveform signal observed from near an interface part of the referencing object as a reference signal in a reference signal storage section;

acquiring in a calculating unit an ultrasonic wave waveform signal acquired at an observation spot of the object corresponding to the observation spot of the reference object and near the interface part to be observed in which a generating time region is limited from a thickness known in advance and a sonic speed of the ultrasonic wave; and comparing and calculating the ultrasonic wave waveform signal acquired from the object and the reference signal to obtain a relative value, and observing the joint state of the boundary face in the calculating unit.

According to a second aspect of the present invention, there is provided the ultrasonic wave measuring method according to the first aspect, wherein a waveform signal is acquired in the calculating unit from an interface within the XY plane of a part or an entire portion of the object, and the reference signal is held in the reference signal storage section as a database of each region in a region specified in the XY plane of a measuring target or is held in the reference signal storage section as a same database in a plurality of regions in the XY plane of the measuring target.

According to a third aspect of the present invention, there is provided the ultrasonic wave measuring method according to the first aspect, wherein the object having the plurality of interfaces is irradiated with the ultrasonic wave, the comparing and calculating is performed in the calculating unit between the waveform signal observed from the object and the reference signal, and quality determination of comparison and calculation result is performed in a determining section using a quality determination threshold set in advance as a reference.

According to a fourth aspect of the present invention, there is provided the ultrasonic wave measuring method according to the first aspect, wherein the object having the plurality of interfaces is irradiated with the ultrasonic wave, the comparing and calculating is performed in the calculating unit between the waveform signal observed from the object and the reference signal, and a time phase difference generated for every observed waveform signal is corrected in the calculating unit by having a point where the two waveform signals best match as a reference point.

According to a fifth aspect of the present invention, there is provided the ultrasonic wave measuring method according to the first aspect, wherein the object having the plurality of interfaces is irradiated with the ultrasonic wave, the comparing and calculating is performed in the calculating unit between the waveform signal observed from the object and the reference signal, a time phase difference generated for every observed waveform signal is corrected in the calculating unit by having a point where the two waveform signals best match as a reference point, and thereafter quality determination is performed in a determining section by comparing waveform components within a predetermined time region in the XY plane specified in advance.

According to a sixth aspect of the present invention, there is provided the ultrasonic wave measuring method according to the first aspect, wherein the object having the plurality of interfaces is irradiated with the ultrasonic wave, the comparing and calculating is performed in the calculating unit between a short interval region waveform signal and a short interval region reference signal, obtained by dividing the waveform signal observed from the object and the reference signal respectively into a plurality of regions in a time direction, and values of calculation result in the respective regions are compared in a determining section.

According to a seventh aspect of the present invention, there is provided an ultrasonic wave measuring apparatus for irradiating with an ultrasonic wave an object to be detected having a plurality of interfaces, detecting a waveform signal generated from the object, and observing a joint state of a boundary face of the object, the ultrasonic wave measuring apparatus comprising:

an ultrasonic wave transmission and reception device for irradiating with the ultrasonic wave the object and detecting the waveform signal generated from the object;

a reference signal storage section for saving, for every observation spot of a reference object which cross-sectional structure, material, and thickness are the same as the object in a certain specific region within an XY plane orthogonal to a direction of irradiating with the ultrasonic wave, an entire waveform signal of the reference object or a waveform signal observed from near an interface part of the referencing object, as a reference signal; and a calculating unit for acquiring an ultrasonic wave waveform signal acquired at an observation spot of the object corresponding to the observation spot of the reference object and near the interface part to be observed in which a generating time region is limited from a thickness known in advance and a sonic speed of the ultrasonic wave, and comparing and calculating the ultrasonic wave waveform signal acquired from the object and the reference signal to obtain a relative value, and thus, observing the joint state of the boundary face.

According to an eighth aspect of the present invention, there is provided the ultrasonic wave measuring apparatus according to the seventh aspect, wherein the calculating unit performs, after irradiating with the ultrasonic wave the object having the plurality of interfaces, the comparison and calculation between the waveform signal observed from the object and the reference signal; and the apparatus further comprises, a determining section for performing quality determination of a comparison calculation result using a quality determination threshold set in advance as a reference.

According to the above-described measurement method, quality (good or bad) determination is accurately performed by canceling the phase difference created for every detected object or for every region of the detected object, and comparing with a reference signal obtained from a reference object, which is an example of an acceptable article.

Effects of the Invention

According to the present invention, there are obtained effects in that the phase difference generated for every observed object or for every region to be observed is canceled, quality does not only rely on the amplitude intensity, and automatic determination can be carried out at high accuracy by making a comparison with an acceptable article.

BRIEF DESCRIPTION OF DRAWINGS

These and other aspects and features of the present invention will become clear from the following description taken in conjunction with the preferred embodiments thereof with reference to the accompanying drawings, in which:

FIG. 1A is a view showing an outline of an ultrasonic wave measuring apparatus for performing quality determination according to a first embodiment of the present invention;

FIG. 1B is a block diagram of a control unit and the like of the ultrasonic wave measuring apparatus for performing quality determination according to the first embodiment of the present invention;

FIG. 6 is a view describing the determination method using the correlation coefficient according to the first embodiment (in FIG. 6, unit of vertical axis in each of "acquired waveform" graph and "master data" graph is arbitrary intensity value and horizontal axis of each of them is time (μs), the vertical axis of "correlation coefficient value" graph is correlation value (−1 to 1 etc.), and the horizontal axis thereof is number "m" of data points);

FIG. 9 is a view describing the cutout of the waveform for time phase correction in the second embodiment (in FIG. 9. unit of vertical axis is arbitrary intensity value and the horizontal axis is time (μs)) in each of the "acquired waveform" graph and the "master data" graph);

FIG. 14 is a view describing a determination method with the short interval master data in which the time phase correction is not performed according to a fourth embodiment (unit of vertical axis is arbitrary intensity value and the horizontal axis is time (μs));

DETAILED DESCRIPTION OF THE INVENTION

Figure 1C:
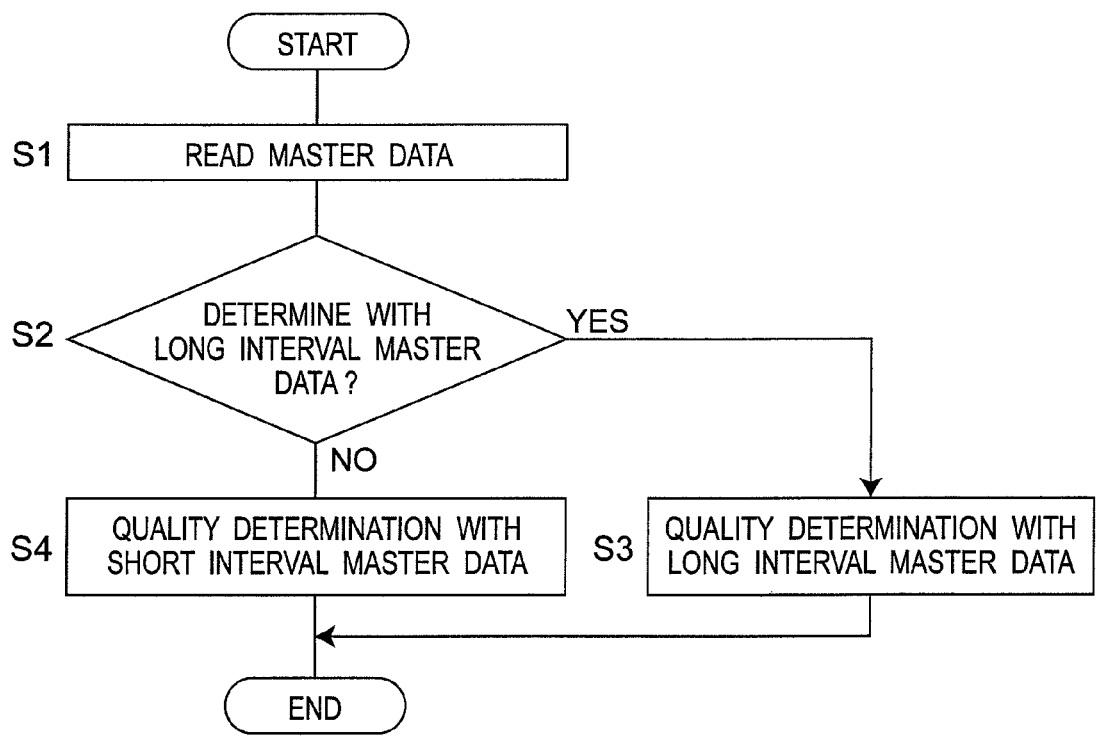
FIG. 1C is a flowchart showing a process of an ultrasonic wave measuring method for performing quality determination according to the first embodiment of the present invention.

Before the description of the present invention proceeds, it is to be noted that like parts are designated by like reference numerals throughout the accompanying drawings.

Embodiments of the present invention will be described in detail with reference to the drawings.

First Embodiment

FIG. 1A, FIG. 1B, and FIG. 1C are views showing a detailed configuration of an ultrasonic wave measuring apparatus for performing quality (good or bad) determination according to a first embodiment of the present invention, a control unit of the ultrasonic wave measuring apparatus, and a flowchart showing a process of an ultrasonic wave measuring method using the ultrasonic wave measuring apparatus.

The ultrasonic wave measuring apparatus of FIG. 1A is configured including an ultrasonic probe 1, an ultrasonic probe drive unit 1a, a control unit 4, and an input section 6. In FIG. 1A, the scanning area listed as an item to be set refers to setting what range of the sample to measure (XY plane position). For instance, entire surface of the sample, or one part of the sample (see scanning area 2Sa of sample 2, which is a first example of the scanning area of FIG. 1G), or a plurality of areas (see scanning areas 2Sb of sample 2, which is a second example of the scanning area of FIG. 1H) may be provided in the sample. The scanning pitch refers to a mechanical resolution (XY plane) for acquiring the waveform data. As one example, the data can be acquired at a pitch of several μm to 100 μm, but is not limited thereto. See FIG. 16 and third embodiment, to be hereinafter described, for the trigger position, the trigger width, the gate position, and the gate width. They refer to a signal (trigger signal) for specifying a reference position of an observation time signal, and an observation starting position signal (gate signal) having a time offset from the reference signal.

The ultrasonic probe 1 has the lower end thereof arranged in water 3 in a water tank 3a, and can irradiate, with an ultrasonic wave having a frequency band of about 10 to 100 MHz, an observed object (object to be observed) 2 arranged at a predetermined arrangement position of the observed object in the water 3 in the water tank 3a with water 3 as a medium, and can receive the reflected wave reflected by the observed object 2.

The ultrasonic probe drive unit 1a is configured by an XY robot for moving the ultrasonic probe 1 in the X direction and the Y direction along the plane parallel to the bottom surface of the water tank 3a and being orthogonal to each other. The ultrasonic probe 1, the ultrasonic probe drive unit 1a, a transmission circuit 30, and a reception circuit 31, to be hereinafter described, configure one example of an ultrasonic wave transmission and reception device.

The control unit 4 is connected with the ultrasonic probe 1, the input section 6, and an output section 5.

The input section 6 is an instrument enabling a worker to input information necessary for ultrasonic wave measurement such as numerical values using various input devices such as keyboard, mouse, touch panel, or voice input, or an instrument including a connection terminal with another server or a database such as a recording medium for inputting information necessary for ultrasonic wave measurement such as CAD data of the observed object 2, and position coordinate data of the arrangement position of the observed object in the water tank.

The output section 5 is configured by a display serving as one example, and performs a predetermined calculation and determination based on the information received by a data processing section 33, to be hereinafter described, of the control unit 4, and then, displays the imaged determination result on the display.

The control unit 4 includes the transmission circuit 30, connected to the ultrasonic probe 1, for emitting ultrasonic wave; a pulsar receiver (the reception circuit) 31, connected to the ultrasonic probe 1, for converting the ultrasonic wave received by the ultrasonic probe 1 to voltage, and amplifying the same; an A/D circuit 32, connected to the reception circuit 31, for converting a signal of the received reflected wave to digital information; and a data processing section 33, inputted with the digital information from the A/D circuit 32, for performing a predetermined data processing (e.g., imaging of intensity value of the observed waveform). The control unit 4 also includes a measurement position data memory 37; and a drive control section 38, connected to the ultrasonic probe drive unit 1a and the measurement position data memory 37, for drive-controlling the ultrasonic probe drive unit 1a based on the information stored in the measurement position data memory 37.

The data processing section 33 includes a master data holding memory 36 serving as one example of a reference signal storage section for storing in advance the master data that becomes the reference signal of the ultrasonic reflected waveform; a data calculating unit 34 serving as one example of a calculating section, connected to the master data holding memory 36 and the A/D circuit 32, for performing calculation based on the information stored in the master data holding memory 36 and the digital information from the A/D circuit 32; and a determining unit 35, connected to the data calculating unit 34, for performing quality (good or bad) determining operation based on the calculation result in the data calculating unit 34.

The observed object 2 is irradiated with the ultrasonic wave generated from the ultrasonic probe 1 with the water 3 as a medium under the drive control of the transmission circuit 30 and the drive control section 38 of the control unit 4. The wave reflected from the observed object 2 is received by the ultrasonic probe 1, and the ultrasonic wave reception signal is converted to voltage and then amplified in the reception circuit 31 of the control unit 4 based on the information received in the ultrasonic probe 1, converted to digital information in the A/D circuit 32, and then inputted to the data calculating unit 34 of the data processing section 33. Waveform processing, image processing, and the like are carried out in the data calculating unit 34, so that quality determination of the interface of the observed object 2 and imaging of the determination result are carried out in the determining unit 35. The imaged determination result is displayed on the display serving as one example of the output section 5.

The ultrasonic probe 1 is used for both transmission and reception.

The observed object serving as the detected object (object to be detected) is targeted on that in which a different interface is provided on the interface to be observed (position to measure), and the ultrasonic wave is reflected at the respective interfaces. In other words, the observed object 2 is an object with a plurality of interfaces, where the waveform signal generated by irradiating with an ultrasonic wave is detected, and the joint state of the boundary face of the plurality of interfaces is observed.

Figure 17A:
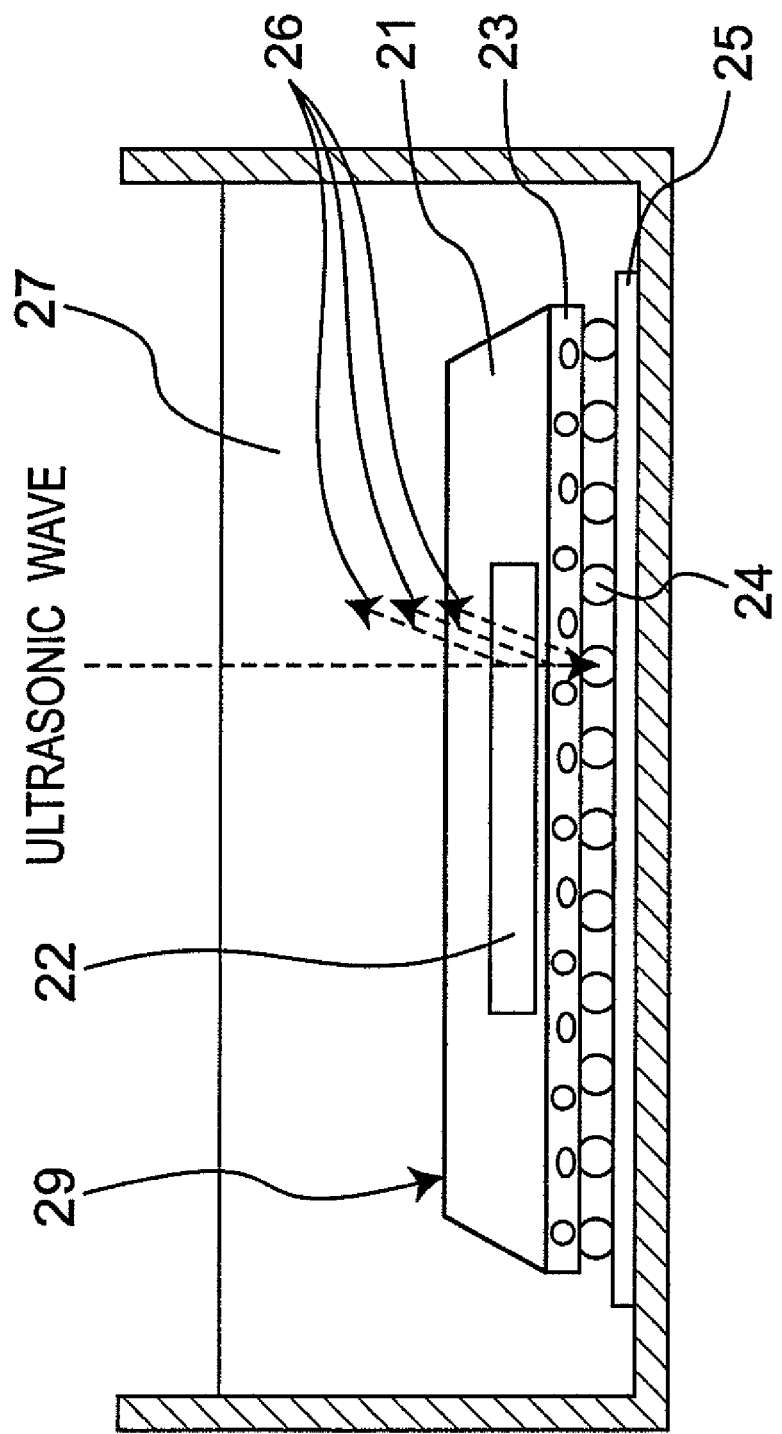
FIG. 17A is a view showing an example of an observed object arranged in water in a water tank.
Figure 17B:
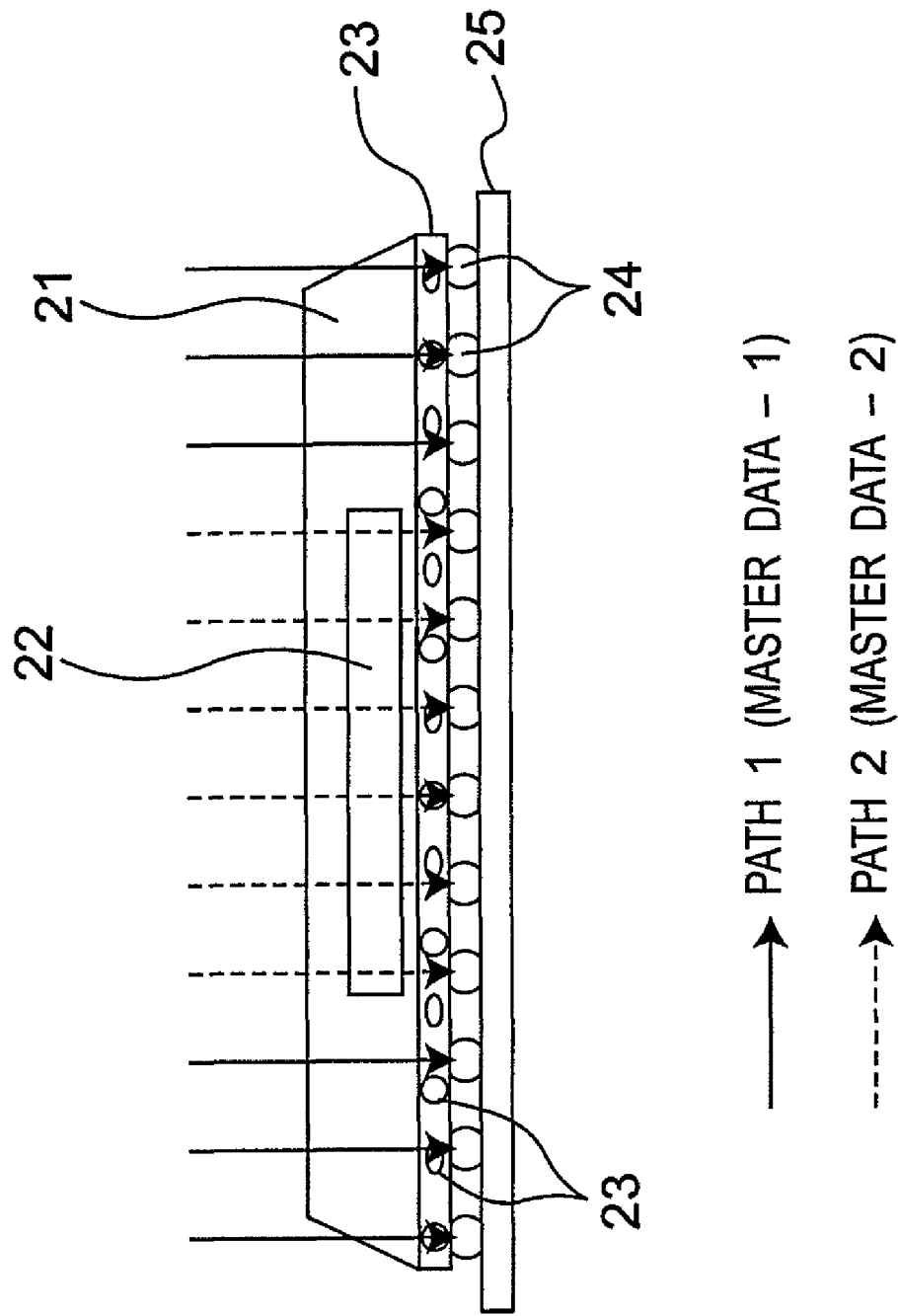
FIG. 17B is a view describing a path of an ultrasonic wave on the observed object.
Figure 18:
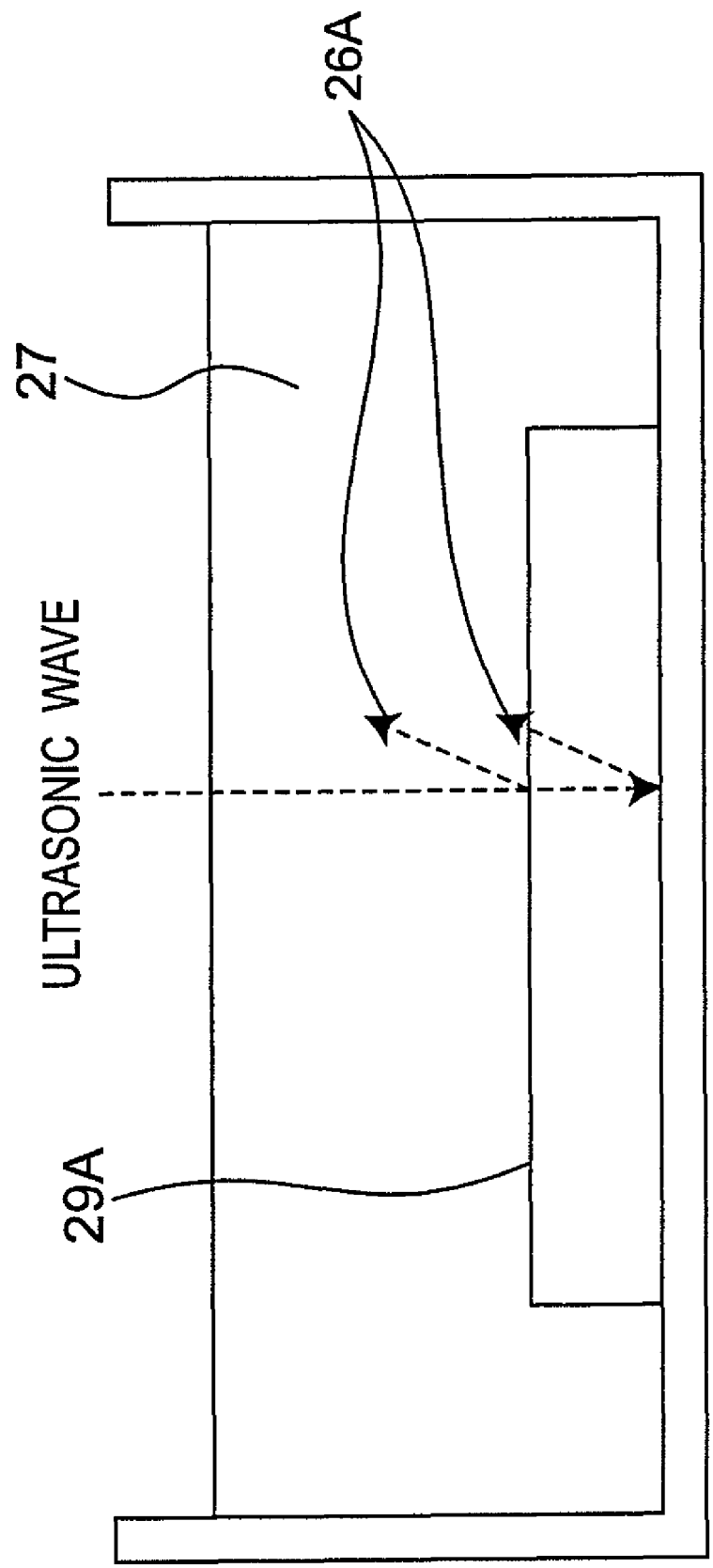
FIG. 18 is a view showing an example of another observed object.

An electronic package 29 such as a semiconductor chip, as shown in FIG. 17, is assumed as a specific example of the observed object 2. The ultrasonic wave transmits through the interior of the observed object 2, so that the reflected wave is also generated from the interior interface. Therefore, the signal received by the ultrasonic probe 1 has a waveform in which a plurality of waves generated from the plurality of interfaces overlap each other.

As shown in FIG. 10, the ultrasonic wave measuring method of the first embodiment stores in advance the master data that becomes the reference signal of the ultrasonic reflected waveform in the master data holding memory 36, and performs quality determination of the observed object 2 that serves as the detected object in the determining unit 35 with the master data stored in the master data holding memory 36 as a reference. At a pre-stage (stage before starting measurement) before performing the following steps, information on the master data condition (starting time position, time width, short interval time position, short interval time width, etc.) of the waveform signal are inputted from the input section 6 and stored in the master data holding memory 36 so that the master data of the waveform signal is created in advance in the master data holding memory 36, as shown as one example in FIG. 2.

First, in step S1, the master data of the waveform signal stored in the master data holding memory 36 such as information on the master data condition (starting time position, time width, short interval time position, short interval time width, etc.) of the waveform signal are read into the data calculating unit 34. At least one needs to be an acceptable observed object (sample) in order to create the master data. Since the master data becomes the database, no problems will arise even if the master data is changed or the number of master data is increased after a predetermined time has elapsed from the actual start of the observation.

The acceptable observed object (sample) refers to a reference object for quality determination in which the cross-sectional structure, material, and thickness in a certain specific region within the XY plane orthogonal to the direction of irradiating with the ultrasonic wave are the same as the observed object 2.

However, if the observed object 2 is changed or the ultrasonic flaw detection conditions are changed, the master data needs to be re-acquired. Here, "change in the observed object" refers to change etc. in thickness of each layer and/or sonic speed of the observed object 2. Furthermore, "change in ultrasonic flaw detection conditions" refers to movement of the focus position of the probe, change in damping resistance value, change etc. of the filter band, or change in the shape of the waveform signal itself when acquiring the reflected signal.

In relation to creating the master data, the master data needs to be acquired for every XY plane if a different structure exists in a Z direction orthogonal to the XY directions when observing a certain observed object 2 within the XY plane. For instance, in the electronic package 29 shown in FIG. 17B, two paths can be considered depending on whether or not to pass an Si semiconductor chip 22 when observing the solder joint part (solder bump) 24. In other words, a path from the resin mold layer 21 to the solder joint part 24 through the interposer layer 23 (23a is conductive particle) may be set as the first path. A path from the resin mold layer 21 to the solder joint part 24 through the Si semiconductor chip 22 and the interposer layer 23 may be set as the second path. Two of such paths exist in the same electronic package 29. In this case, the time the ultrasonic wave arrives at the solder joint part 24 differs between the first path and the second path. Moreover, the reflected waveform also differs between the first path and the second path due to attenuation etc. of the ultrasonic wave by the Si semiconductor chip 22. Therefore, the master data needs to be changed between the first path and the second path.

Next, the actual measurement of the observed object 2 can be carried out after the master data of the waveform signal is read into the data calculating unit 34 (step S1) and ready for data processing. Whether to determine with a long interval master data or to determine with a short interval master data is selected (step S2). For instance, a method of determining with the long interval master data (step S3) is selected if variation in the correlation coefficient value by the set long interval master data is small. If variation in the correlation coefficient value by the set long interval master data is large, a method of determining with the short interval master data (step S4) is selected in which the phase difference is corrected with the long interval master data and then the short interval master data is created therefrom, and determination is carried out.

The method of determining with the long interval master data (step S3) is described in the first embodiment, and the method of determining with the short interval master data (step S4) is described in the second embodiment.

Figure 1D:
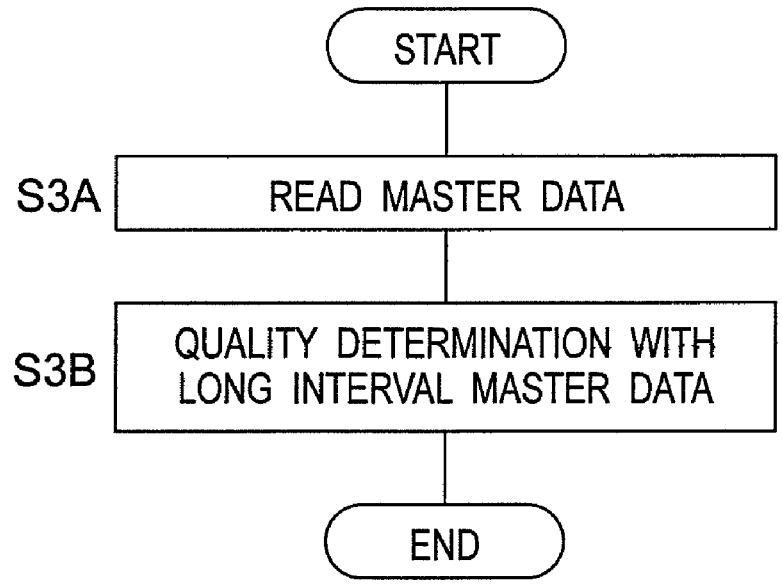
FIG. 1D is a flowchart showing a process of a method of determining with the long interval master data in the ultrasonic wave measuring method for performing quality determination according to the first embodiment of the present invention.

FIG. 1D is a flowchart showing a schematic process of the method of determining with the long interval master data (step S3), where the waveform of the long interval master data is first read to the data calculating unit 34 (step S3A), and thereafter, quality determination with the long interval master data is performed (step S3B). The details on the method of determining with the long interval master data (step S3) will be hereinafter described based on FIG. 5.

Figure 1E:
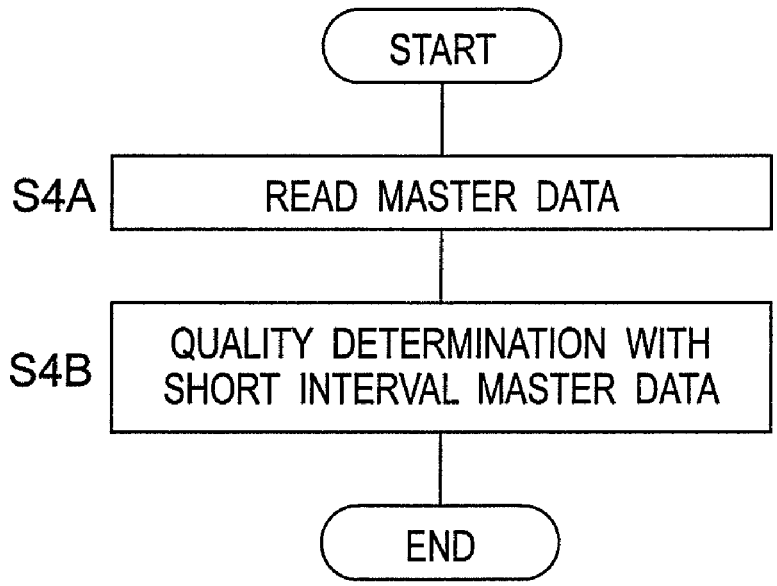
FIG. 1E is a flowchart showing a process of a method of determining with the short interval master data in the ultrasonic wave measuring method for performing quality determination according to the first embodiment of the present invention.

FIG. 1E is a flowchart showing a process of the method of determining with the short interval master data, where the waveform of the short interval master data is first read to the data calculating unit 34 (step S4A), and thereafter, quality determination with the short interval master data is performed (step S4B). The details on the method of determining with the short interval master data (step S4) will be hereinafter described based on FIG. 8.

Figure 1F:
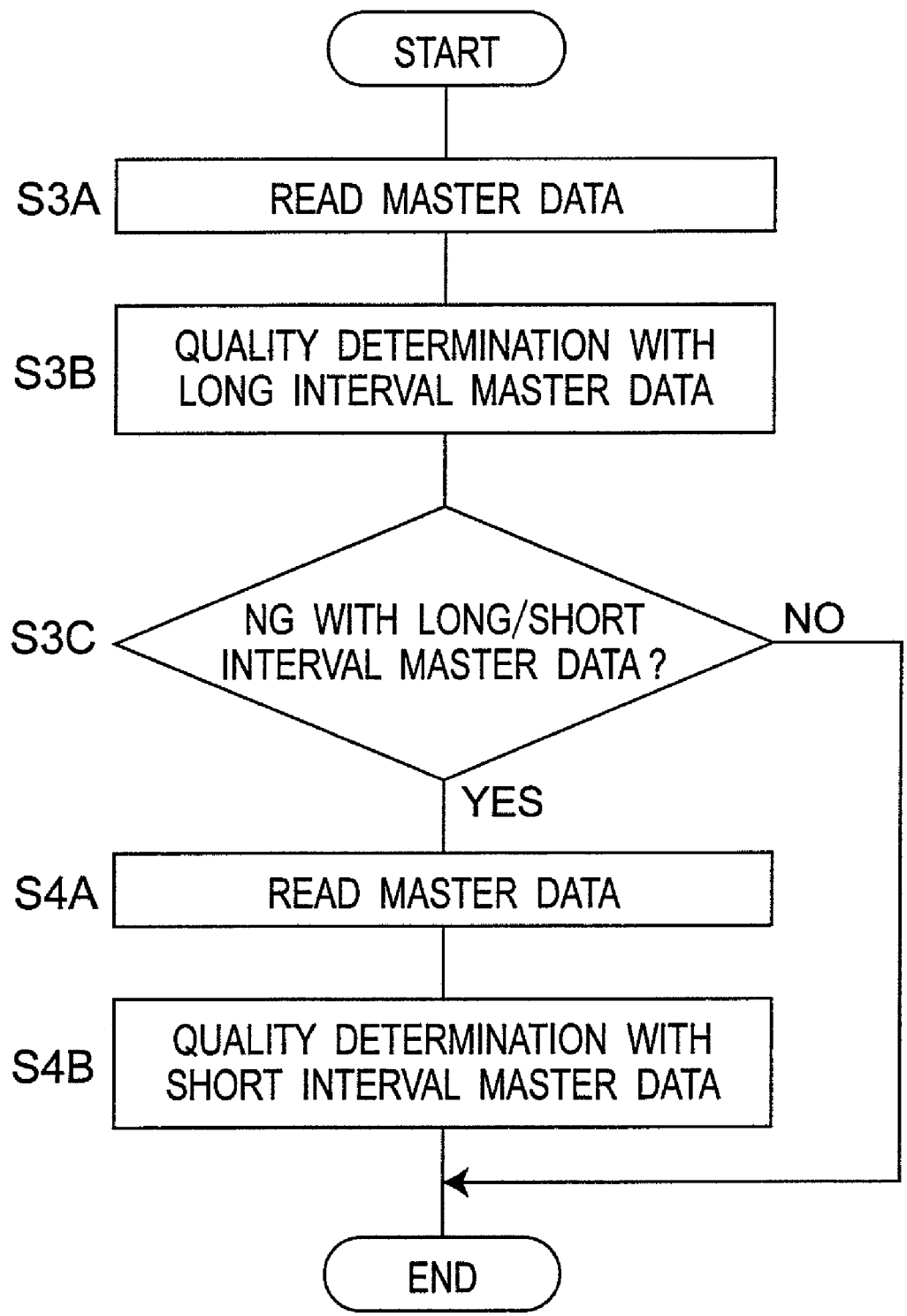
FIG. 1F is a flowchart showing a modified example of a method of determining with the long interval master data in the ultrasonic wave measuring method for performing quality determination according to the first embodiment of the present invention, a process of a method of determining with the short interval master data when object is found in the determination result.
Figure 1G:
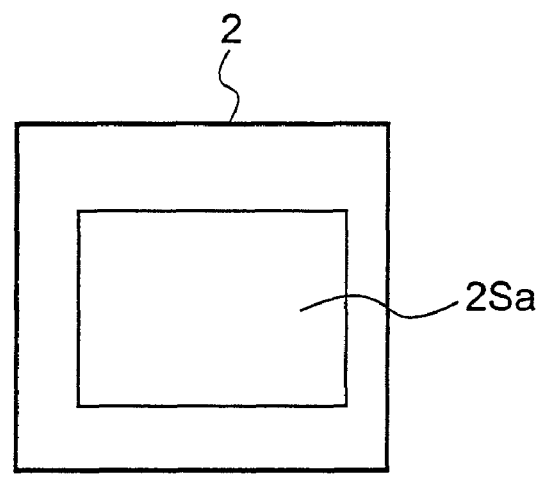
FIG. 1G is an XY plane view in which the entire surface of the sample is a scanning area in a first example of the scanning area for describing the scanning area according to the first embodiment of the present invention.
Figure 1H:
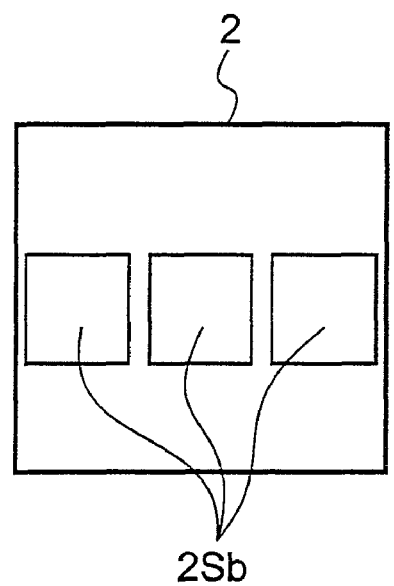
FIG. 1H is an XY plane view in which a plurality of areas in the sample is a scanning area in a second example of the scanning area for describing the scanning area according to the first embodiment of the present invention.

FIG. 1F is a modified example of the method of determining with the long interval master data, that is a flowchart showing a process of the method of determining with the short interval master data when defect is found in the determination result. In other words, the waveform of the long interval master data is read to the data calculating unit 34 (step S3A), and thereafter, quality determination with the long interval master data is performed (step S3B). If determined in the determining unit 35 that defect is not found in the result of quality determination with the long interval master data (step S3C), the process is terminated as it is. However, if determined in the determining unit 35 that the defect is found in the result of quality determination with the long interval master data (step S3C), the waveform of the short interval master data is read from the table created beforehand and saved in the master data holding memory 36 (step S4A), and then quality determination with the short interval master data is performed (step S4B). Determination on whether or not defect is found in the determination result of the determination unit 35 is made in the following manner. As described in the first and the second embodiments, the correlation coefficient value takes a value between −1 and 1. The master data takes a correlation value of 1, and the acceptable article takes a value close to the correlation value of 1, whereas the defective sample takes a value smaller than such a value. Thus, the defective sample can be determined by setting a certain threshold value to the correlation value as a determining condition before the measurement. With regards to the threshold value, a method of taking statistics from various samples, and determining the value of the threshold value may be considered.

Which one of the processes in FIG. 1D to FIG. 1F to use may be changed for every observed object, or may be changed depending on the measurement position (e.g., every electrode) of one observed object 2.

Here, the "method of determining with the long interval master data" refers to a method of specifying the starting time and the ending time of the waveform that becomes the master data when creating the master data, and determining with all the signals (entire reference signal) of the specified time. Furthermore, the "method of determining with the short interval master data" refers to a method of time-dividing the long interval master data, and determining with the master data of the respective short time width.

Figure 2:
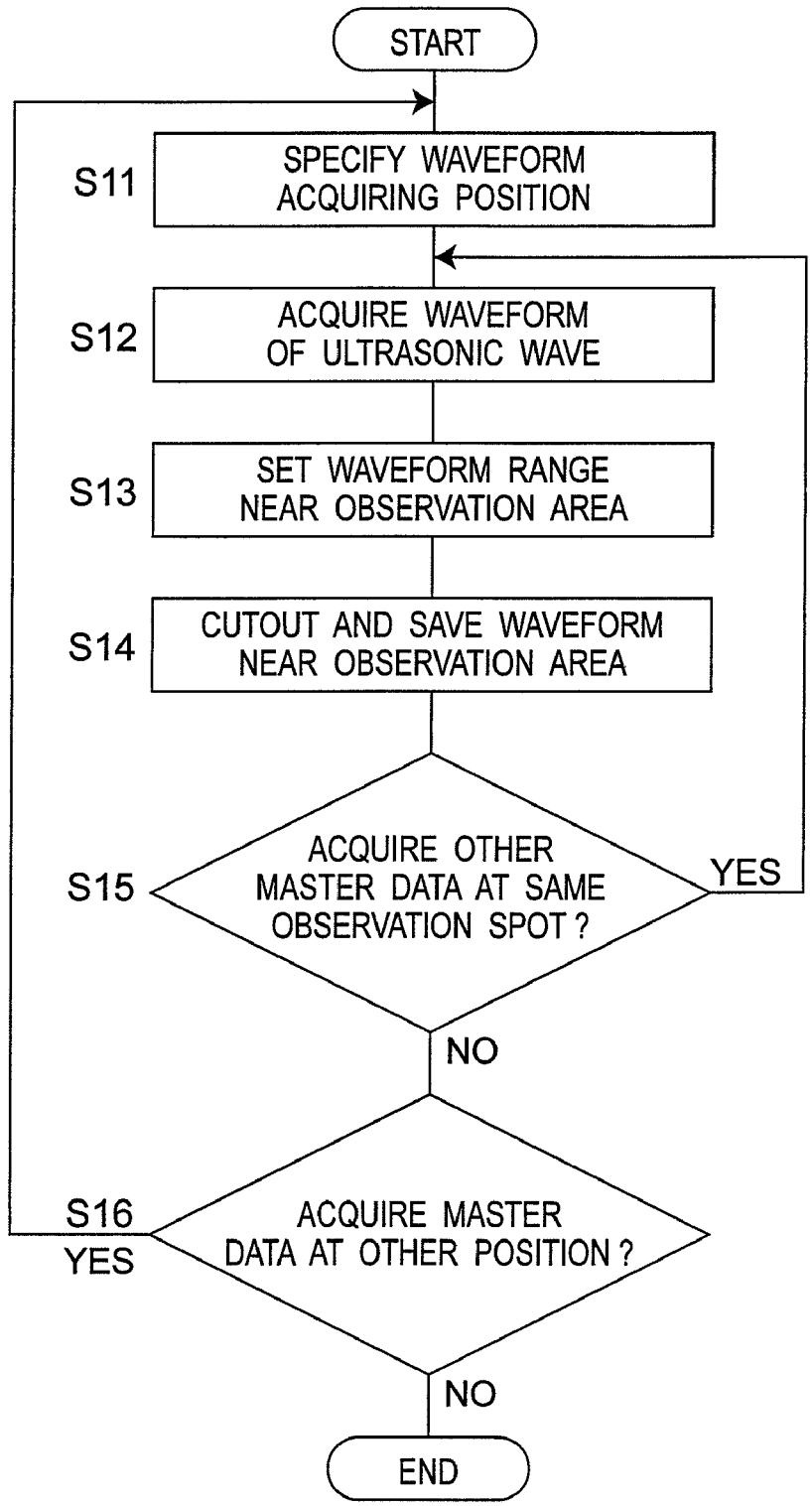
FIG. 2 is a flowchart for creating master data according to the first embodiment of the present invention.
Figure 3A:
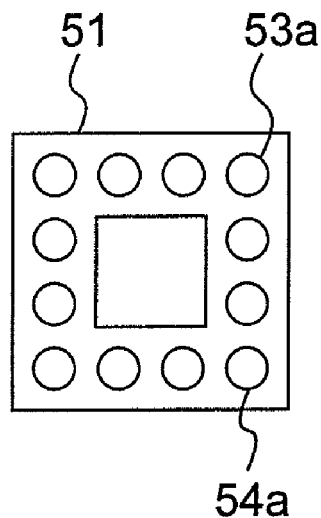
FIG. 3A is an explanatory view of a BGA chip (first sample) that becomes as a master of an acceptable article in the ultrasonic wave measuring method according to the first embodiment.
Figure 3B:
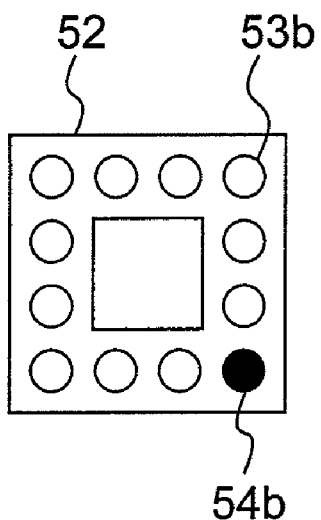
FIG. 3B is an explanatory view of a BGA chip (second sample) or an observed object in the ultrasonic wave measuring method according to the first embodiment.

The description will be specifically made with the flowchart of creating the master data of the waveform data shown in FIG. 2. A case of observing a BGA chip of the electronic package 29 as a sample will be described by way of example. FIG. 3A shows an explanatory view (bottom view) of a BGA chip (first sample) 51 that becomes the master of the acceptable article, and FIG. 3B shows an explanatory view (bottom view) of a BGA chip (second sample) 52 serving as an example of the observed object 2. In FIG. 3A and FIG. 3B, the normal electrode (OK electrode) is indicated with a white circle, and an abnormal electrode (NG electrode) is indicated with a black circle.

First, as shown in FIG. 3A, the BGA chip (first sample) 51 that becomes the master of the acceptable article is prepared, and submerged at a predetermined arrangement position of the observed object in the water 3 of the water tank 3a. From the BGA chip 51 of the acceptable article, the position to measure (measurement position) is specified to the measurement position data memory 37 with the input section 6 (step S11). Specifically, as a method of specifying a coordinate position of the first electrodes 53a, 53b of FIG. 3A and FIG. 3B, the CAD coordinate from which the dimension of the entire electronic package 29 that serves as an example of the observed object 2, and the position coordinate of the electronic package 29 at the arrangement position of the observed object when the electronic package 29 is arranged in the water tank 3, as well as the dimensions and the coordinates of all the electrodes can be found are stored and held in advance in the measurement position data memory 37 of the control unit 4. Alternatively, the CAD coordinate is inputted from the input section 6 to the measurement position data memory 37 and stored therein. In the actual measurement, the coordinates of the specified electrodes such as the first electrodes 53a, 53b out of the coordinates stored in the measurement position data memory 37 are specified in advance to the measurement position data memory 37 by the input section 6, and the ultrasonic probe drive unit 1a is drive-controlled by the drive control section 38 based on the specified coordinates so as to be controlled to a position where the ultrasonic wave can be emitted from the ultrasonic probe 1 with respect to the first electrodes 53a, 53b.

Figure 4:
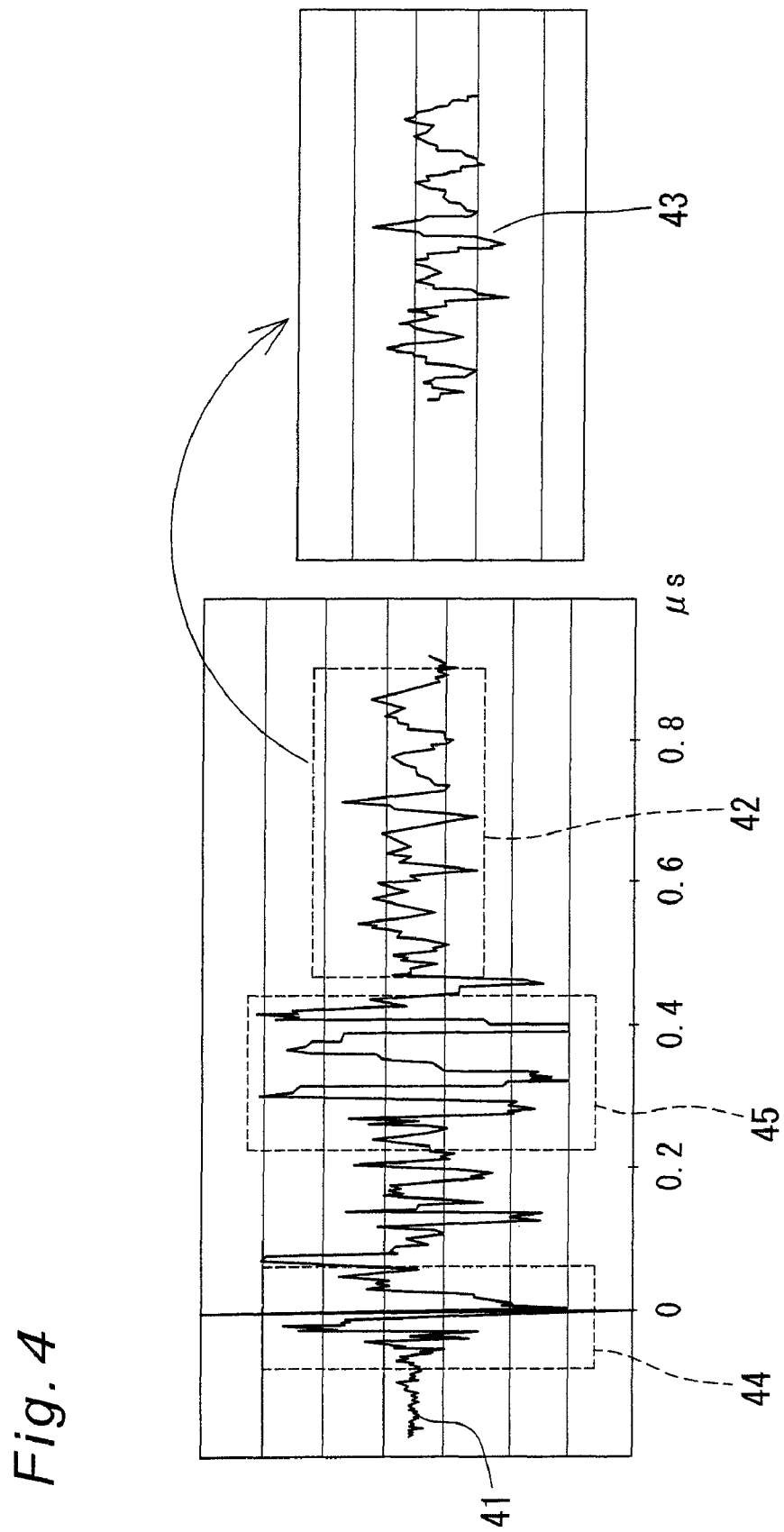
FIG. 4 is a view showing an example of waveform data respectively acquired from the first electrode of the first sample and the first electrode of the second sample according to the first embodiment (unit for vertical axis is arbitrary intensity value, and horizontal axis is time)

The ultrasonic wave is then emitted from the ultrasonic probe 1 towards the first electrodes 53a, 53b, or the position to measure, the reflected waves from the first electrodes 53a, 53b are received at the ultrasonic probe 1, and the waveform data is acquired with the reception circuit 31 (step S12). Here, as an acquiring target of the observed waveform, the first electrodes 53a and 53b of the same position (position on upper right corner in each of FIG. 3A and FIG. 3B) in the first sample 51 of the acceptable article of FIG. 3A and the second sample 52 serving as an example of the actual observed object 2 are respectively taken by way of example. An example of the waveform data acquired from the first electrodes 53a and 53b, respectively, is shown in FIG. 4. Since the first electrodes 53a and 53b are both normal electrodes, the waveform data are the same. With respect to FIG. 4, the ultrasonic wave is received by a piezoelectric element, an analog electrical signal received by the piezoelectric element is A/D converted in an arbitrary unit system, and then digitally outputted. As one specific example, A/D conversion is performed with eight bits (256 levels) with respect to an input range of 1 V, but the general conversion is not limited thereto. The shape of the acquired waveform 41 changes by the number of interfaces etc. through which the ultrasonic wave passes, as described above. Thus, the database needs to be held in the master data holding memory 36 for every position of each electrode, or the position to measure, and the waveform data needs to be compared in the data calculating unit 34. When referring to holding the database for every position of each electrode, this means that information on the conditions such as the master data waveform, the master data dividing method (dividing method for short interval determination), and determination threshold value are held for each observation point of each electrode. Therefore, not only is the master data itself held, but information on the measuring conditions by long interval and short interval, information of the determination threshold value, and the like are also included, and thus it is expressed as a database.

Next, the waveform of the position where information of the interface (e.g., interface of the solder bump 24 and the mother substrate 25 of FIG. 17, and the like) of the observed object 2 is assumed to exist in the acquired waveform 41 is selected by the data calculating unit 34 (step S13), the relevant position is acquired by the data calculating unit 34 as the master data and stored in the master data holding memory 36 (step S14).

As a method of predicting the position where the information exists in the interfaces of the observed object 2, for example, the reflected waveform of the surface of the resin mold is indicated with a reference symbol 44, and the reflected waveform of the interposer layer is indicated with a reference symbol 45 in the waveform shown in FIG. 4. Thus, what waveform is the reflected waveform 44 of the surface of the resin mold or the reflected waveform 45 of the interpose layer can be estimated from time, position, and reflection intensity, and the waveform temporally after the reflected waveform 45 of the interposer layer is selected when determining the interface between the solder bump 24 and the mother substrate 25 of FIG. 17. The information of the master data condition (e.g., starting time position, time width, short interval time position, short interval time width, and the like) of the waveform signal is inputted in advance from the input section 6 to the master data holding memory 36 and stored therein.

Alternatively, if the sonic speed C of the material of each layer (thickness direction) of the sample (electronic package 29) or the observed object 2 and the thickness of each layer are stored in the measurement position data memory 37 and are known, the approximate arrival time of the ultrasonic wave reflected from each interface can be calculated and estimated in the data calculating unit 34 based on the information on the sonic speed C of the material and the thickness of each layer stored in the measurement position data memory 37, and the position where the information exists in the interface of the observed object 2 can be limited by the data calculating unit 34. In other words, the arrival time of the ultrasonic wave can be estimated by the data calculating unit 34 from the data of the measurement position data memory 37, and the time condition thereof is stored in the measurement position data memory 37. In the actual measurement, the arrival time may be automatically called out by the data calculating unit 34 from the measurement position data memory 37 for use. However, since the arrival time changes depending on the accuracy of the sonic speed, and/or, variation in the thickness of each layer, the time width of a certain extent needs to be provided for the master data. As one example, in the example shown in FIG. 4, the waveform length of the acquired waveform 41 is about 900 ns (waveform length reckoned from the trigger acquired position of the surface of the resin mold 21), the reflected waveform 45 of the interposer layer is distributed between about 280 and 480 ns, and thus the master data waveform 43 is set as the position of about 480 ns to 880 ns of the subsequent time, and the length thereof (time width of certain extent) is 400 ns. The interface of the observed object 2 is thus assumed to be contained in the interval of such a length.

Figure 1I:
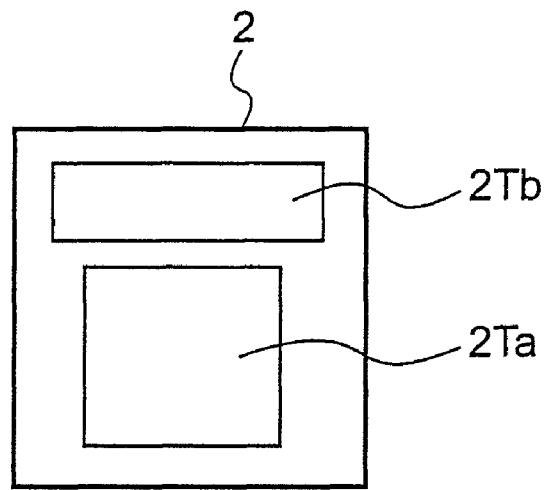
FIG. 1I is an explanatory view for a case where a plurality of observation spots are provided even in one sample if the structure in the Z direction differs to describe the observation spot according to the first embodiment of the present invention.
Figure 1J:
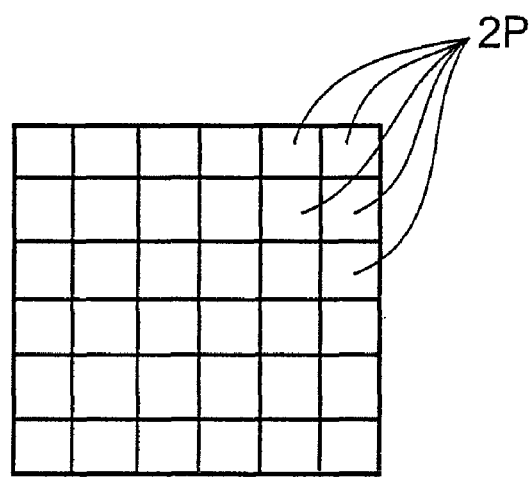
FIG. 1J is an explanatory view for a case where the observation spot has 6×6 observation points to describe the observation spot according to the first embodiment of the present invention.

Next, whether or not to acquire other observation points at the same observation spot (position to measure) is determined (step S15). The observation spot is a spot having the same structure in the Z direction, that is, the depth direction, where the "observation spot" changes if the structure in the Z direction is different. Therefore, if the structure in the Z direction differs even in one sample, a plurality of observation spots exists (see plurality of observation spots 2Ta, 2Tb of sample 2 of FIG. 1I. The structure in the Z direction (direction passing through the plane of drawing of FIG. 1I) differs between the observation spot 2Ta and the observation spot 2Tb), and each observation spot has a database. The observation spot also has a plurality of observation points. Assuming the observation spot has an area of 180×180 μm, and the data acquiring pitch (scanning pitch) is 30 μm, 6×6 data acquiring points are provided as in the plurality of observation points 2P of FIG. 1J. This is called "observation point" (i.e., data acquiring point). The master data described above may take any "observation point" (data acquiring point) as long as it is within one observation spot. However, even if one observation spot has the same depth structure in the Z direction, the waveform may slightly differ for every "observation point" (data acquiring point), in which case, a plurality of "observation points" (data acquiring points) is taken, and processing such as averaging is performed.

As one example of a method of whether or not to acquire other observation points, the data acquiring method may be set in advance in the measurement position data memory 37. For instance, (1) if the acquiring data is one point, the data is acquired from the center of the observation spot; (2) if the acquiring data is X points (X is an integer greater than or equal to 2), the points closest from the center are acquired in order; and (3) if the acquiring data is every point, every points of the observation spot are automatically acquired; where one of (1) to (3) may be set in advance as the data acquiring method in the measurement position data memory 37. In the first electrode 53a, for example, if the diameter of the circular electrode 53a is 300 μm, and the resolution in the X direction of the ultrasonic wave is 30 μm, the waveforms of ten points can be acquired in the x direction. If slight difference in waveform exists in the ten points of the first electrode 53a, such waveforms are averaged in the data calculating unit 34 and held in the master data holding memory 36 serving as the database, where the processing steps S12 to S14 are repeatedly carried out at the same observation spot, and the master data of the waveform data of a plurality of points is extracted and stored in the master data holding memory 36.

Next, if other observation spots exist within a plane including the first electrode 53a of the first sample 51, the master data is created according to the procedure of the processing steps S11 to S15 with the waveform data of the relevant observation spot, and stored in the master data holding memory 36 (Step S16). The observation spot may be a partial or an entire region of the first sample 51.

The master data at the observation spot is created and stored in the master data holding memory 36 in the above manner. The above description is also applicable to the measurement position(s) other than the measurement positions of the electrodes in the first sample 51.

Figure 5:
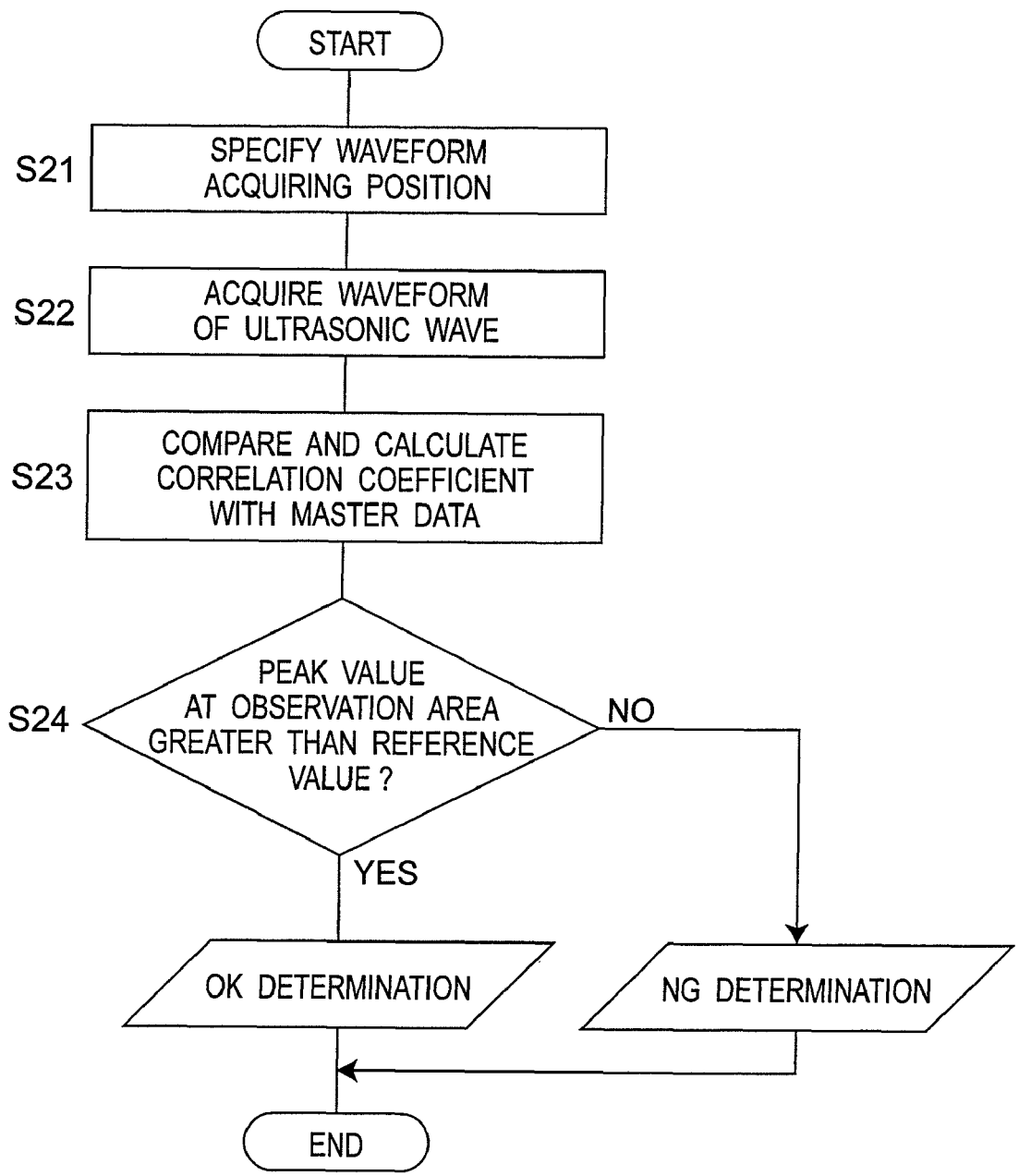
FIG. 5 is a flowchart showing a determination process using the long interval master data according to the first embodiment.

Next, the flowchart of the determination process using the long interval master data shown in FIG. 5 will be described below. The observed object 2 of the BGA chip (second sample) 52 of FIG. 3B is also described here by way of example. The measurement position of the BGA chip (second sample) 52, which is an example of the observed object 2, is specified in the measurement position data memory 37 by the input section 6 (step S21). The specifying manner is the same as step S11.

Next, the ultrasonic wave is emitted from the ultrasonic probe 1 towards the measurement position of the second sample 52, the wave reflected from the measurement position of the second sample 52 is received by the ultrasonic probe 1, and then, the waveform data is acquired by the reception circuit 31, similar to step S12 (step S22).

Next, the comparison calculation of the master data of the first sample 51 stored in the master data holding memory 36 and the waveform data of the second sample 52 inputted and acquired from the A/D circuit 32 is carried out in the data calculating unit 34 (step S23).

One example of the comparison method by the data calculating unit 34 includes taking the correlation coefficient value of the waveform data acquired as the master data. In performing the comparison of the first electrode 53a, if the waveform data of the master in the first electrode 53a of the first sample 51 is data columns $x_1, x_2, \ldots, x_n$, and the waveform data acquired from the first electrode 53a of the second sample 52 is data columns $y_1, y_2, \ldots, y_n$, the sample average of such data is $$\bar{x}, \bar{y} \qquad \text{[Equation 1]}$$

where the correlation coefficient value $r_{xy}$ of x and y can be expressed with the following equation (equation 2).

$$r_{xy} = \frac{\sum_{i=1}^{n}(x_i - \bar{x})(y_i - \bar{y})}{\sqrt{\sum_{i=1}^{n}(x_i - \bar{x})^2}\sqrt{\sum_{i=1}^{n}(y_i - \bar{y})^2}} \qquad \text{[Equation 2]}$$

-continued
$$= \frac{(\text{COVARIANCE OF } x \text{ AND } y)}{(\text{STANDARD DEVIATION OF } x) \times (\text{STANDARD DEVIATION OF } y)}$$

FIG. 6 shows the determination method using the correlation coefficient. Suppose the length of the data column of the waveform data acquired as the master data is N and the length of the data column of the master data is n, (note that N>n). The first point of the waveform data inputted and acquired from the A/D circuit and the first point of the master data stored in the master data holding memory 36 are matched in the data calculating unit 34, and the correlation coefficient value described above is calculated in the data calculating unit 34 with the points up to the n-th point. Next, in the data calculating unit 34, the master data is shifted to the right by one point, and the correlation coefficient value is calculated in the data calculating unit 34 at the (n+1)-th point from the second point of the acquired waveform data. Similarly, the shift to the right by one point and the calculation of the correlation coefficient value are repeatedly carried out in the data calculating unit 34, and the correlation coefficient values from the first point to the {N−(n+1)}-th point of the waveform data are obtained in the data calculating unit 34.

Figure 7A:
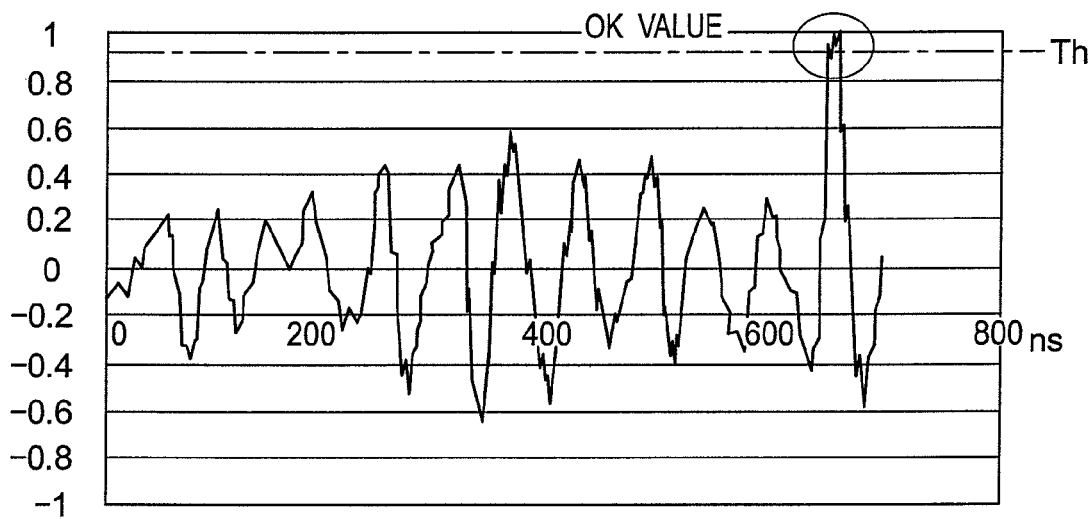
FIG. 7A is a view showing a correlation coefficient waveform of the second electrode (acceptable article) of the first sample in the first embodiment.
Figure 7B:
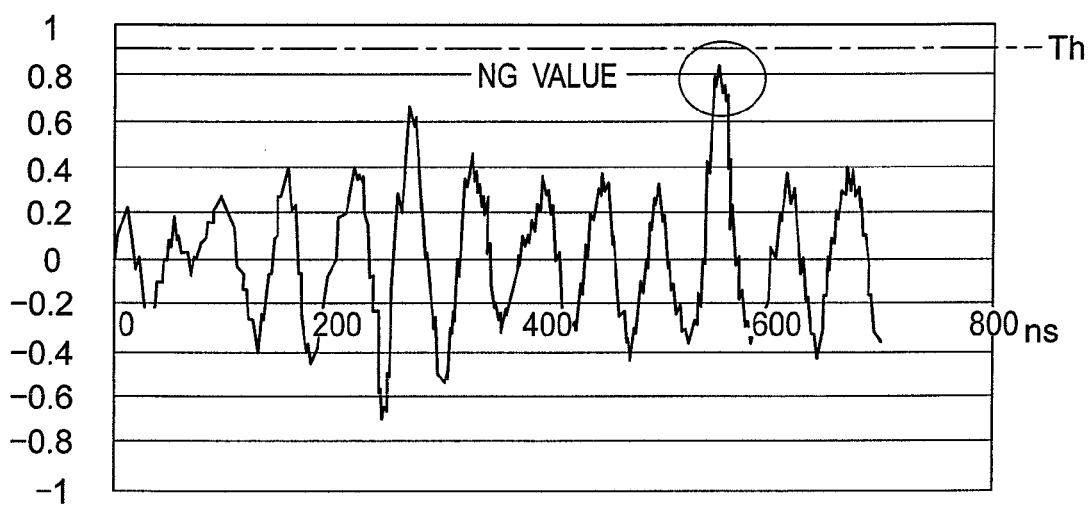
FIG. 7B is a view showing a correlation coefficient waveform of the second electrode (defective article) of the second sample in the first embodiment.

The data column of m column ($1 \leq m \leq \{N-(n+1)\}$) is created in the data calculating unit 34 by shifting the master data by 1, 2, ..., N−(n+1) points. FIG. 7A shows a correlation coefficient waveform of the second electrode 54a (acceptable article) of the first sample 51, and FIG. 7B shows a correlation coefficient waveform of the second electrode 54b (defective article) of the second sample 52.

The master data is retrieved from the acquired signal waveform of the first electrode 54a of the first sample in the data calculating unit 34 and stored in the master data holding memory 36. The specification of the data position containing the information of the interface or the measuring target within the signal waveform is carried out by acquiring the largest value (maximum value) of the correlation coefficient value peak in the data calculating unit 34. However, the spectrum may become the largest at the data position not containing the information of the interface to measure, in which case the data range is specified in advance in the data calculating unit 34 (e.g., waveform region 42 near the measurement position shown in FIG. 4), and the information of the spectrum is acquired in the data calculating unit 34.

As described above, when specifying the data position containing the information of the interface or the measuring target, comparison is made with the waveform value of the maximum value of the plurality of correlation coefficient value peak values of FIG. 7A, or the time interval is narrowed down and then, the maximum value of the correlation coefficient value peak values within the narrowed time interval is retrieved. The maximum value is automatically acquired by the data calculating unit 34. The subsequent determination is also automatically performed in the determining unit 35 after providing a quality determination threshold value to the determining unit 35 in advance.

In FIG. 7A, the data interval is narrowed to 600 to 800 points, and the spectrum value is acquired in the data calculating unit 34. The number of data points and the ultrasonic wave waveform time axis have relevance, and thus the data interval to narrow down can be estimated from the ultrasonic wave waveform time axis in the data calculating unit 34. The correlation coefficient value at each point takes a value of from −1 to 1, where the signal waveform of the acceptable article close to the master data is obtained the closer the value is to 1, and the observed object 2 can be said as an acceptable article in that correlation is achieved. The correlation coefficient value of the signal waveform not achieving correlation becomes close to zero. If the correlation is achieved with the signal waveform in opposite phase, the value becomes closer to −1.

The first sample 51 is the sample from which the master data is acquired, and thus the correlation coefficient waveform of the master data and the acquired waveform itself has a peak value at 1. The correlation coefficient value in the second sample 52 of the defective article is between 0.68 and 0.81 in view of variation in the electrode in the second electrode 54b (i.e., NG electrode) of the second sample 52 shown in FIG. 7B. Since some kind of waveform change exists in the second sample 52 of the defective article, the correlation coefficient value lowers. Thus, the determination of OK/NG is performed in the determining unit 35 with a certain correlation coefficient value as the quality determination threshold value (e.g., threshold value Th of FIG. 7A and FIG. 7B) (step S24). In other words, the NG determination is made in the determining unit 35 if smaller than the threshold value of the certain correlation coefficient value, and the OK determination is made in the determining unit 35 if greater than or equal to the threshold value of the certain correlation coefficient value. Regarding the threshold value, n number of samples to use are obtained (i.e., prepare N (N is an integer greater than or equal to one) samples of the same structure (type) and obtain the data), the average of the acceptable articles and the defective articles is obtained, and the threshold value is determined in the determining unit 35 and saved in the master data memory 36. The threshold value is necessary only when performing the acceptable article determining operation, and the threshold value is unnecessary when only measuring the correlation value without performing the acceptable article determining operation. For example, the value input from the input section 6 to the determining unit 35 may be used for the threshold value.

If the plurality of waveform data is acquired for the master data in the processing step S15 of FIG. 2 described above, for example, the above-described determination may be performed over plural times at the same observation spot. In other words, if n master data are held at the same location (here, n is an integer greater than or equal to two), the second determination is performed in the determining unit 35 with the second master data before outputting NG if determined as NG in the first determination in the determining unit 35. The function of allowing the above determinations up to n-th time, which corresponds to the number of master data being held, may be provided to the determining unit 35. The number of determinations, the selecting method of the master data, the determination reference, and the like in this case may be arbitrarily set with respect to the determining unit 35 by the user using the input section 6 in the method of the first embodiment.

If a plurality of waveforms is acquired for the master data in the processing step S15 of FIG. 2, a method of storing and holding the result of addition-averaging the master data in the data calculating unit 34 (addition-averaged master data) in the master data holding memory 36 as one master data, and performing the above-described determination in the determining unit 35 using the addition-averaged master data being stored and held may be adopted.

Thus, the method of comparing the peak value of the correlation coefficient waveform obtained from the acceptable article sample and the observed value in the data calculating unit 34, and determining the sample with small value as the defective article in the determining unit 35 is the feature of the first embodiment of the present invention.

According to the first embodiment, the phase difference generated for every observed object or for every region to be observed is cancelled, quality does not rely only on the amplitude intensity, and the automatic determination can be carried out at high accuracy by making a comparison with the acceptable article.

Second Embodiment

An ultrasonic wave measuring method and an apparatus therefor according to a second embodiment of the present invention will be described below.

Determination may be difficult in some cases in the determination method described in the first embodiment. If the range of variation of the correlation coefficient value is the range of the correlation coefficient value of the acceptable article and the defective article such as if the variation is large in the correlation coefficient value by the set long interval master data, the determination is not possible. The reason may be that the length of the master data is inappropriate, or that information other than OK/NG of the interface is contained in excess.

For instance, the master data width in FIG. 4 is 400 ns, but if the magnitude of one wave is about 60 ns and the change in waveform in time of defect is worth one wave, the master data contains an overly excessive waveform component. In this case, even if defect occurs and the waveform changes by one wave, the information on such change in waveform is buried in the excessive waveform component and distinction may not be made between the defective article and the acceptable article for the correlation coefficient value. Thus, in a case where the master data having a very short master data width such as a width of 60 ns corresponding to the magnitude of one wave in the above case is used for the master data, difference with the acceptable article is created in the correlation coefficient value during the occurrence of defect. The master data which width is much shorter than the master data of the first embodiment in such a manner is referred to as the short interval master data.

The long interval master data refers to the entire reference signal created in advance, and refers to the data obtained by cutting out the vicinity of the reflected signal of the interface to be measured, from the reflected time signal. The short interval master data, on the other hand, refers to the data obtained by time-dividing the long interval master data, and corresponds to each element. The example of the dividing method will be hereinafter described.

Figure 19:
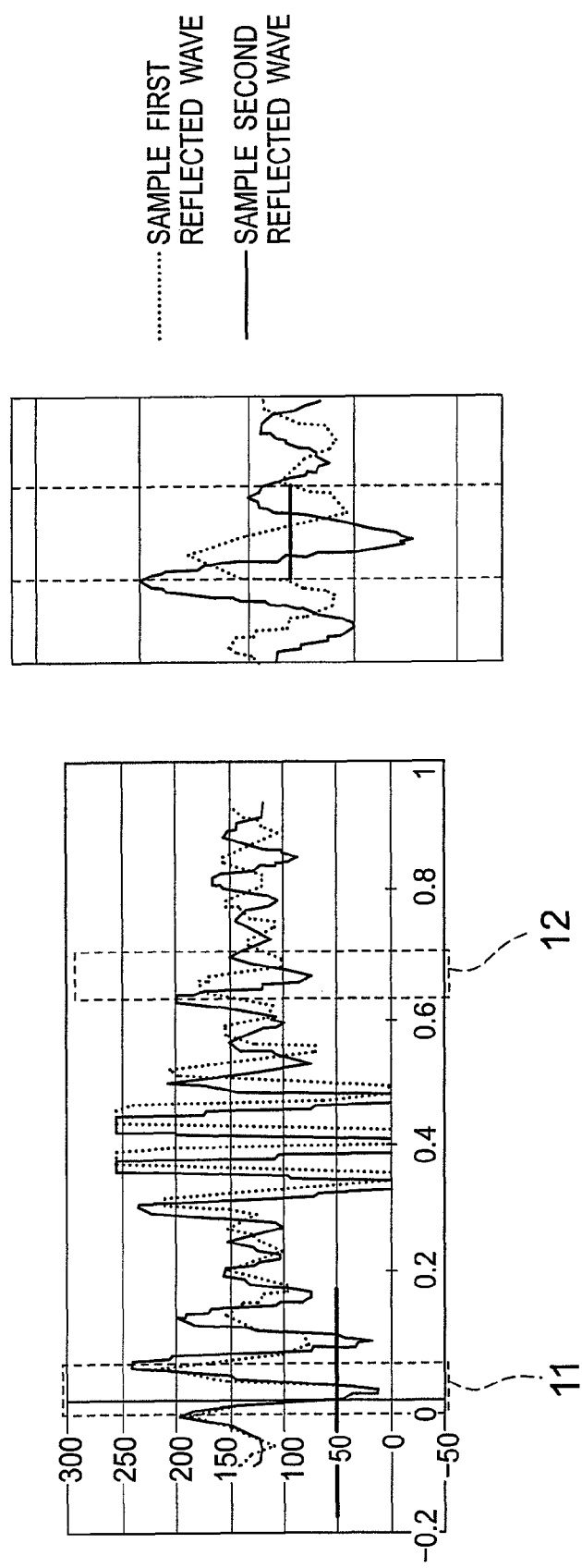
FIG. 19 is a view describing occurrence of time phase difference after triggering the surface for every sample.
Figure 20A:
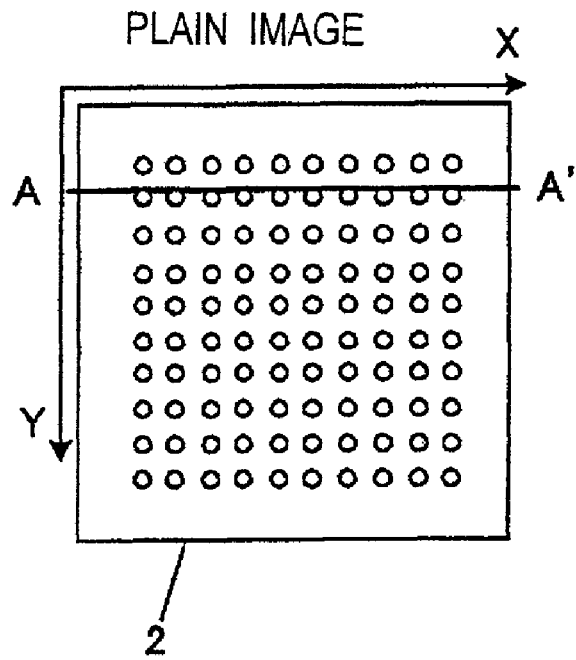
FIG. 20A is a view showing a C-scope image of a semiconductor chip when an interposer layer is made of glass epoxy resin.
Figure 20B:
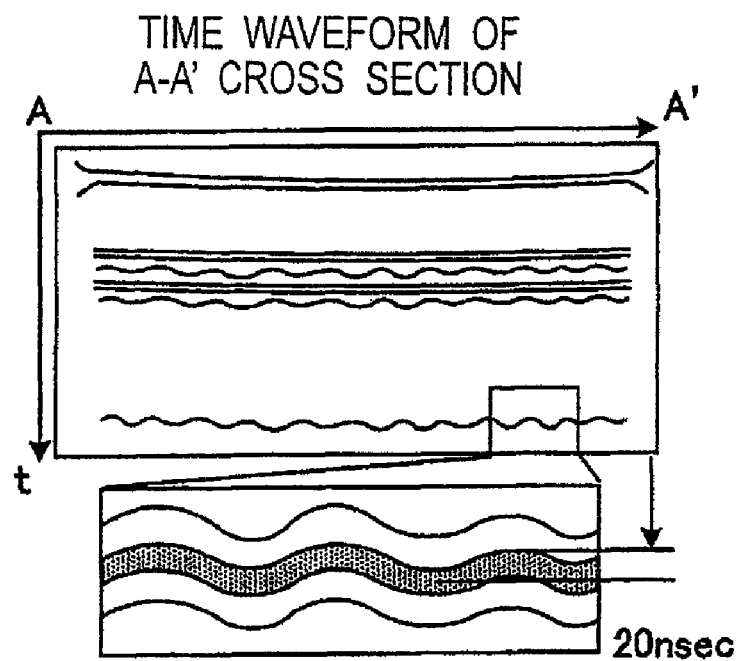
FIG. 20B is a view showing a B-scope image at a cross-sectional portion taken along line A-A' of FIG. 20A of the semiconductor chip when the interposer layer is made of glass epoxy resin.
Figure 21:
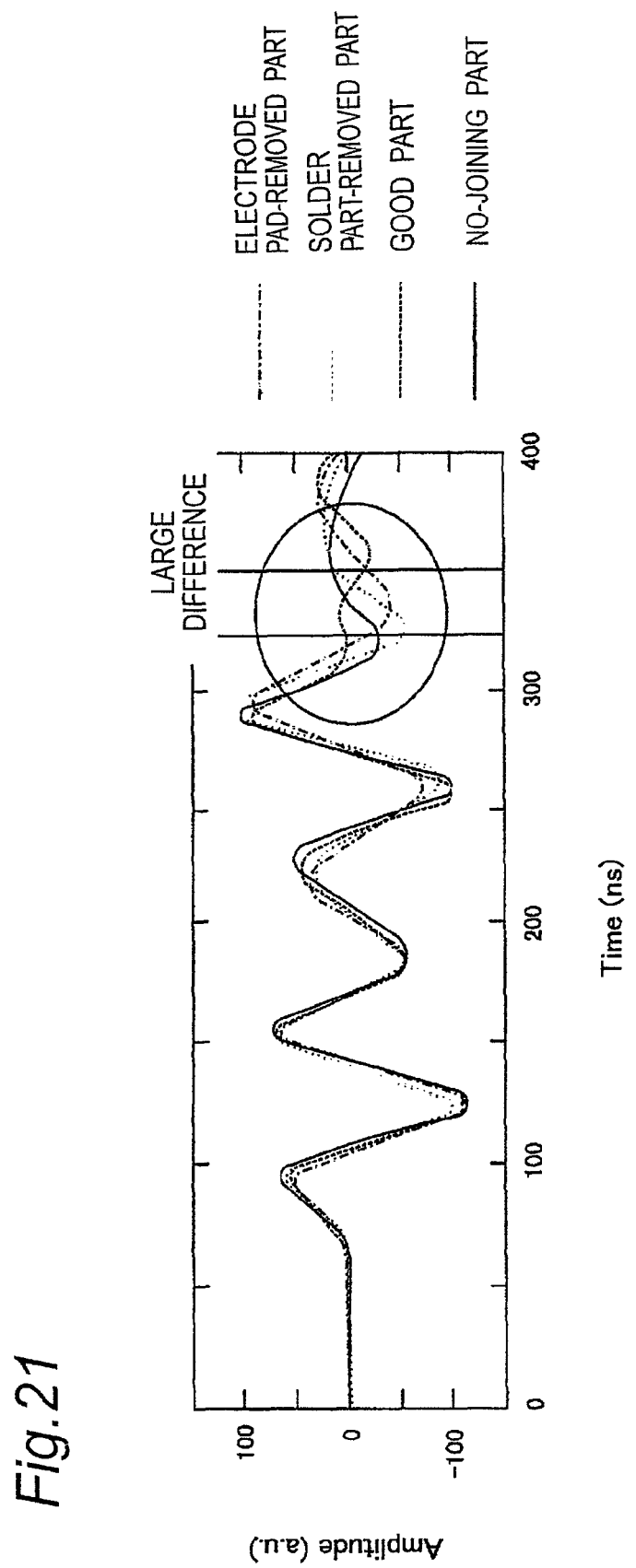
FIG. 21 is a view showing occurrence of waveform difference after a predetermined time has elapsed.

However, if tasks as described in FIG. 6 are performed with the short interval master data, a plurality of similar locations may be captured in the observed acquired waveform, and may be outputted as the correlation coefficient waveform. As shown in FIG. 19, FIG. 20A, and FIG. 20B, the phase difference may appear at a time after the surface trigger position depending on the observed object 2, and thus the data position of the correlation coefficient value becomes indefinite at the interface to be measured in the short interval master data. Information on the interface to be measured becomes difficult to obtain from the correlation coefficient value waveform with simple short interval master data.

Figure 8:
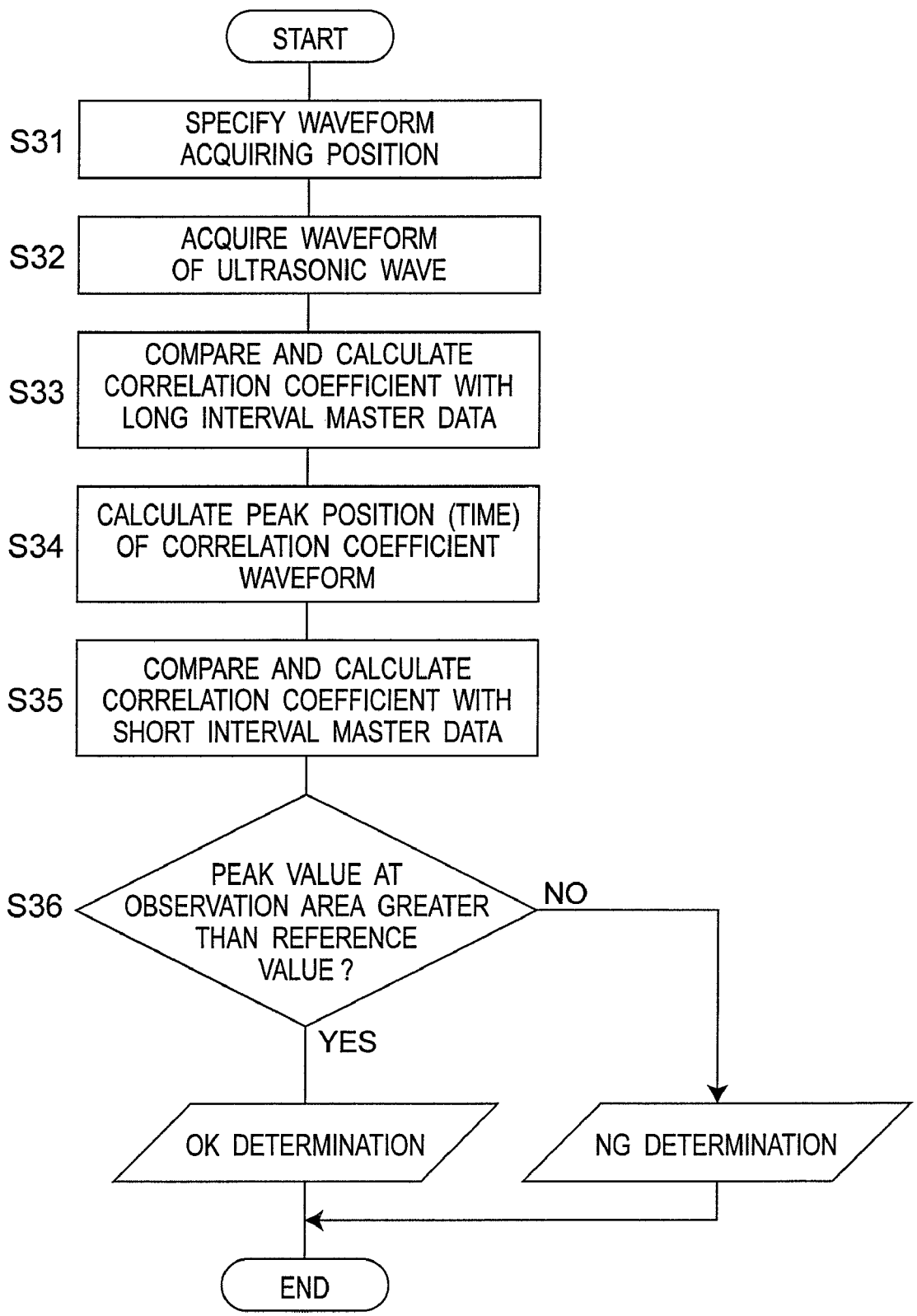
FIG. 8 is a flowchart showing a determination method using the short interval master data according to a second embodiment.

In order to solve such an issue, a determination method with the short interval master data (master data of short time region) including time phase correction will be described as the second embodiment of the present invention. FIG. 8 shows a flowchart for performing the determination process with the short interval master data.

As a rough process, the time phase correction is performed with the long interval master data in the first stage (steps S31 to S34), and quality determination is performed with the short interval master data in the second stage (steps S35, S36). Similar to the determining operation with the long interval master data described above, the BGA chips (first and second samples) 51, 52 of FIG. 3A and FIG. 3B are used as examples of the observed object 2.

The time phase correction by the long interval master data in the first stage is a process substantially the same as the determination process with the long interval master data of the first embodiment. The measurement position of the second sample 52 of the observed object 2 is specified with the specifying method similar to step S11 (step S31).

Next, the ultrasonic wave is emitted from the ultrasonic probe 1 towards the measurement position of the second sample 52, the wave reflected from the measurement position of the second sample 52 is received by the ultrasonic probe 1, and the waveform data is acquired with the method similar to step S12 (step S32).

Then, the comparison of the master data of the first sample 51 and the acquired waveform data of the second sample 52 is performed in the data calculating unit 34 using the correlation coefficient (step S33).

Thereafter, the data position that becomes a spectrum peak (interface to measure) of the correlation coefficient waveform by the long interval master data is acquired in the data calculating unit 34 (step S34).

Next, FIG. 9 is a view describing a cutout of the waveform for correcting time phase according to the second embodiment. As shown in FIG. 9, the acquired waveform is cutout in the data calculating unit 34 at the data position where the spectrum of the correlation coefficient by the long interval master data and the observed and acquired waveform becomes the peak (step S34). The spectrum peak of the correlation coefficient is a time axis on which the acquired waveform is similar to the long interval master data. That is, when observing different samples of the same type, even if a slight time phase difference is created every time the acquired waveform is obtained, the waveform data of the interface to be measured can always be cutout in the data calculating unit 34 by acquiring the position of the peak value of the correlation coefficient waveform spectrum.

A manner of searching the spectrum peak in the interface to be measured includes taking the largest correlation coefficient value in the peak values in the data calculating unit 34 in FIG. 7A by way of example. Obviously, the time region in which acquired waveform is the most similar to the master data may be supposed to have a large spectrum peak value.

However, in some cases, the maximum peak may not be necessarily obtained at the waveform position of the interface to be measured, or a significant difference between the spectrum peak of the interface to be measured and the spectrum peak of another interface may be small. In this case, a method of limiting, in advance, the time range at the position of the spectrum peak of the interface to be measured in the data calculating unit 34 may be considered.

For instance, if the range of variation of the phase time difference for every sample is verified as about 40 ns, the observed correlation coefficient spectrum is also acquired in the data calculating unit 34 within a range of about ±40 ns. Alternatively, a method of counting the spectrum peak from the head time in the data calculating unit 34, and specifying the spectrum peak of the interface to be measured in the data calculating unit 34 may be considered.

Quality determination with the short interval master data is then performed as the second stage.

Figure 10A:
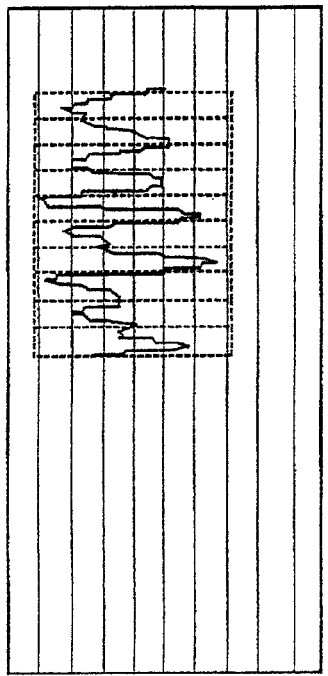
FIG. 10A is a view describing the determination with the short interval master data according to the second embodiment, that is a view of a state in which the cutout acquired waveform is segmentalized (unit of vertical axis is arbitrary intensity value and the horizontal axis is time (μs))
Figure 10B:
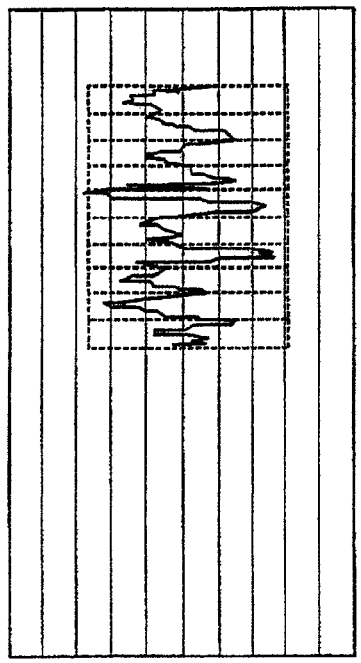
FIG. 10B is a view describing the determination with the short interval master data according to the second embodiment, that is a view of a state in which the master data waveform is segmentalized (unit of vertical axis is arbitrary intensity value and the horizontal axis is time (μs))

First, the long interval master data is segmentalized and divided in the data calculating unit 34 to obtain the short interval master data, and the correlation coefficient value is obtained in the data calculating unit 34 (step S35). Here, FIG. 10A is a view describing the determination of the short interval master data according to the second embodiment, that is a view of a state in which the cutout acquired waveform is segmentalized, and FIG. 10B is a view describing the determination of the short interval master data according to the second embodiment, that is a view of a state in which the master data waveform is segmentalized. For instance, in FIG. 10A and FIG. 10B, the time width of the long interval master data is 400 ns, and the short interval master data is created therefrom in the data calculating unit 34. A segmentalizing method (dividing method) includes segmentalization using dividing number, master data time width, or the like. The dividing number or the time width differs according to the frequency component of the waveform, the extent of influence on the waveform at the occurrence of the defective article, or the like. Fast Fourier transformation is performed in the data calculating unit 34 on the entire or the partial waveform of the long interval master data, and an optimum time width may be set in the data calculating unit 34 after acquiring the frequency spectrum in the data calculating unit 34. One example of setting the optimum time width includes the setting of the following manner. An ultrasonic transducer outputs a wave having a certain frequency band for every transducer (in this case, the sensor itself needs to be changed in order to change the frequency band). The frequency band is observed, the cycle of the generated waveform is calculated, and the time width may be set from the cycle. Specifically, if the center frequency of the spectrum obtained by the Fourier transformation of the observed signal waveform is F (MHz), the cycle T of such a waveform becomes T=1/F (μs). Then, for example, the optimum time width can be obtained by having the width of the cycle or the width of the cycle of two times or three times as the time width of short interval.

Figure 10C:
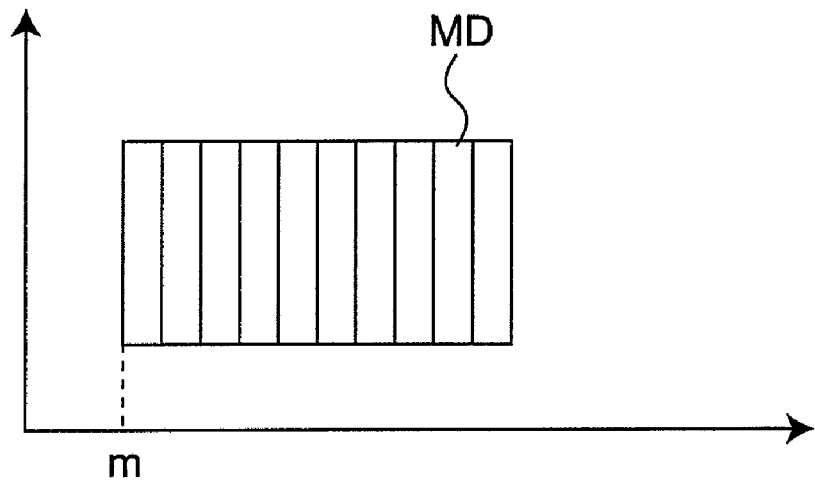
FIG. 10C is a view describing calculation of the correlation value at time point m matching in the long interval master data to describe the time search width in the second embodiment (for the sake of simplifying the illustration, waveform as in FIG. 10A is omitted and only the frame of the master data is shown, but actually, the waveform as in FIG. 10A is within the frame of the master data)
Figure 10D:
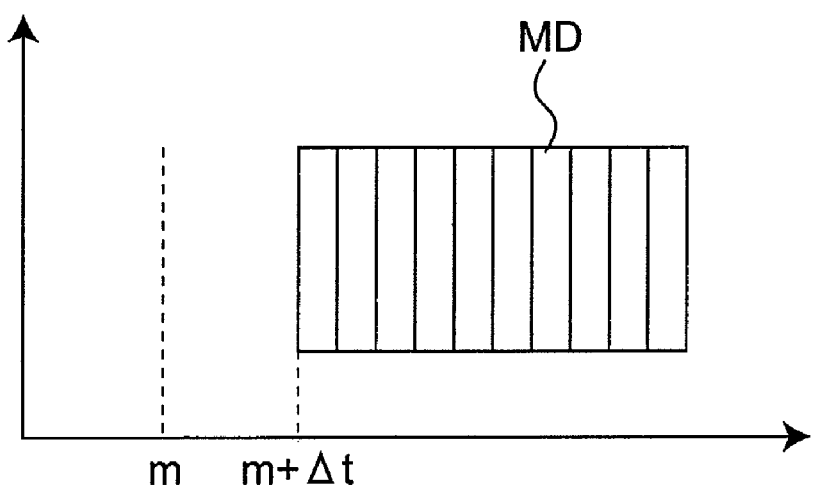
FIG. 10D is an explanatory view for a case where the master data MD is shifted by Δt points from time point m as a retry determination after the calculation of the correlation value in FIG. 10C to describe the time search width in the second embodiment (for the sake of simplifying the illustration, waveform as in FIG. 10A is omitted and only the frame of the master data is shown, but actually, the waveform as in FIG. 10A is within the frame of the master data)
Figure 10E:
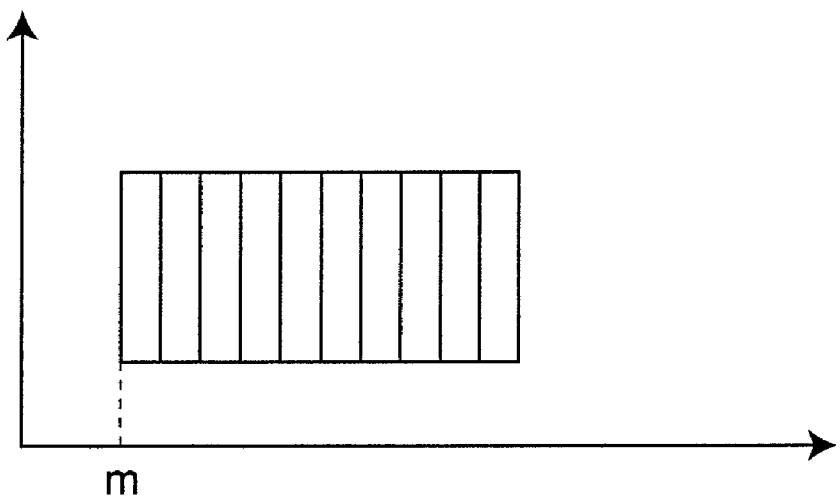
FIG. 10E is a view describing calculation of the correlation value at time point m matching in the long interval master data to describe the time warping rate in the second embodiment (for the sake of simplifying the illustration, waveform as in FIG. 10A is omitted and only the frame of the master data is shown, but actually, the waveform as in FIG. 10A is within the frame of the master data)
Figure 10F:
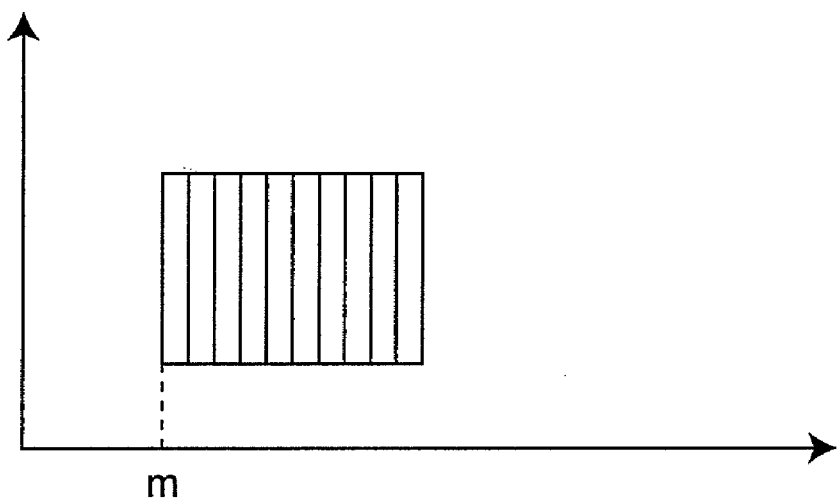
FIG. 10F is an explanatory view for a case of performing the calculation by compressing the master data in the X % (X is a preset value) time direction as a retry determination after the calculation of the correlation value in FIG. 10E to describe the time warping rate in the second embodiment (for the sake of simplifying the illustration, waveform as in FIG. 10A is omitted and only the frame of the master data is shown, but actually, the waveform as in FIG. 10A is within the frame of the master data)

The time width does not necessarily need to be made constant, and the lengths may be differed between the short interval master data in which only the time width of the m short interval master data (here, m is an integer smaller than n) of n divisions (here, n is an integer of greater than or equal to two) is 20 ns, and the time width of the other (n-m) short interval master data is 40 ns. The segmentalizing method is saved in advance in the memory in the data calculating unit 34 as a set value before the measurement. In addition to the dividing number or the time width described above, the information of the short interval master data includes, for example, a time search width, a time warping rate, and the like of the short interval master data. The set value of the short interval master data is changed as needed by the value set in advance in the data calculating unit 34 for every observation to obtain the optimum set value in the data calculating unit 34. Regarding the time search width, after calculating the correlation value at a time point m matched in the long interval master data, the master data MD may be shifted by Δt point from the time point m (e.g., shifted by Δt point from the time point m as shown in FIG. 10C to FIG. 10D), and calculation with the short interval master data may be performed again (see FIG. 10C and FIG. 10D), as a retry determination. The width of Δt of the retry in this case is defined as the time search width. Regarding the time warping rate, after calculating the correlation value at time point m matched in the long interval master data, the master data may be compressed by X % (X is a preset value) in the time direction (e.g., reduced by X % in the time direction as shown in FIG. 10E and FIG. 10F) and then, the calculation may be performed (see FIG. 10E and FIG. 10F), as a retry determination. The compression rate of the master data in the retry in this case is defined as the time warping rate. In a method of obtaining an optimum set value in the data calculating unit 34, for example, a certain regularity (e.g., regularity of an extent of setting the search width, the warping rate, the dividing number, or the like to a certain arbitrary number) appears when the data setting of the short interval master data is changed for every observation. The set data in this case may be stored in a library.

As some kind of change in waveform is found in the correlation coefficient value obtained in the processing step S35, the correlation coefficient value lowers. Thus, the OK/NG determination is performed in the determining unit 35 with a certain correlation coefficient value as a threshold value (step S36). In other words, the NG determination is performed in the determining unit 35 if smaller than the threshold value of the certain correlation coefficient value, and the OK determination is performed in the determining unit 35 if greater than or equal to the threshold value of the certain correlation coefficient value. The manner of setting the threshold value is similar to step S24.

The correlation coefficient value of FIG. 10A showing the waveform cutout from the long interval master data and FIG. 10B showing the short interval master data is taken. In this case, with respect to the short interval master data, the correlation coefficient waveform by the shift as in FIG. 6 is not calculated, but instead, the correlation coefficient value with each short interval master data is obtained in the data calculating unit 34 at the data position of FIG. 10A in the time phase corrected and cutout state. In other words, the acquired waveform cutout from the long interval master data is segmentalized in the data calculating unit 34, and with respect to each of the short interval master data obtained by segmentalizing the long master data based on the set value in the data calculating unit 34, the correlation coefficient is obtained in the data calculating unit 34. By way of example, in FIG. 10B, the long interval master data (width of 400 ns) is divided by ten (width of 40 ns) in the data calculating unit 34 and the acquired waveform cutout by dividing into ten parts is obtained, and similarly in FIG. 10A, the data is divided by ten in the data calculating unit 34 and the correlation coefficient of each short interval master data component is calculated in the data calculating unit 34 (calculate ten correlation coefficient values in the data calculating unit 34).

Figure 11A:
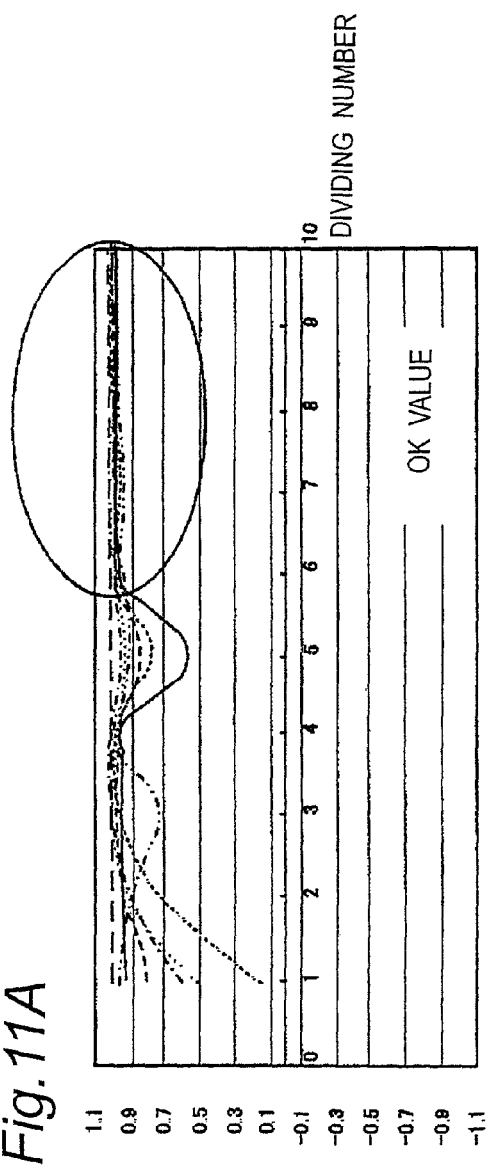
FIG. 11A is a view showing a correlation coefficient waveform of a second electrode (acceptable article) of the first sample in the second embodiment.
Figure 11B:
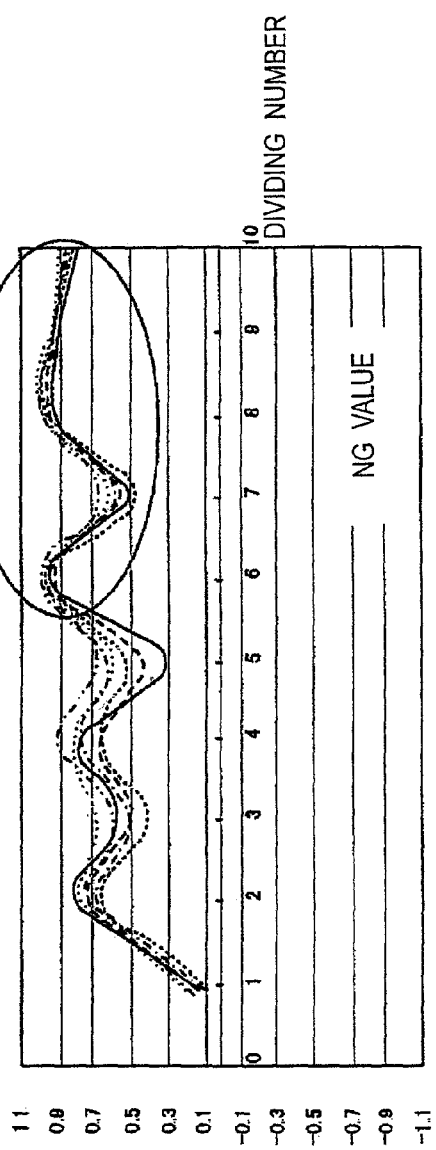
FIG. 11B is view showing a correlation coefficient waveform of a second electrode (defective article) of the second sample in the second embodiment.

FIG. 11A shows a correlation coefficient value in each short interval master data of the second electrode 54a (see FIG. 3A) of the first sample 51, and FIG. 11B shows a correlation coefficient value in each short interval master data of the second electrode 54b (see FIG. 3B) of the second sample 52, and respectively displays the correlation coefficient values at ten points as the master data is divided by ten. The number of points is shown in the order of fastest time (order from left) in the segmentalized short interval master data. With respect to the correlation coefficient value of the first sample 51 (acceptable article) shown in FIG. 11A, a large significant difference is found in the seventh short interval master data in the correlation coefficient value of the second sample 52 (defective article) shown in FIG. 11B.

In FIG. 11A and FIG. 11B, the seventh short interval master data of the segmentalized correlation coefficient values is given attention for the following reasons.

First, in FIG. 9, the first large waveform of reflection (see square frame I) is the wave reflected from the surface of the resin mold 21, and the waveform (see square frame II) immediately before the cutout waveform is the wave reflected from the surface of the interposer layer 23. This can be easily predicted from the order of layer structure of the electronic package 29. The reflected wave after the waveform of the square frame II (i.e., reflected wave after the surface of the interposer layer 23) is the long interval master data.

In the example of FIG. 9, the thickness of the interposer layer 23 is 350 μm and the sonic speed is 2800 m/s. Thus, the time when the ultrasonic wave passes the interposer layer 23 becomes (350×2)/2800=0.250 μs (however, the obtained time is the reciprocate time in which the ultrasonic wave passes the interposer layer twice in the outward and the homeward directions, and thus (thickness of interposer layer×2) is used.

The width of the long interval master data is 400 ns, the segmentalized width is 40 ns, and thus 40×7=280 ns, whereby the reflected wave of the lower surface of the interposer layer 23 returns to the seventh segmentalized width. The joint surface is the joint surface of the solder bump 24 and the interposer layer 23, that is, the position to measure. Thus, the seventh segmentalized width is given attention.

In some cases, the significant difference may become large compared to the significant difference in the determination with the long interval master data described above. For instance, the long interval master data cannot be determined if the difference in the OK/NG waveform can be observed only in a certain interval of 40 ns. Even if at which time region the interval where such a waveform difference appears is not known, the change in waveform can be seen in the correlation coefficient plot by the short interval master data. Even if the waveform difference of the reflected waves from the OK/NG samples is about one wave, the difference is actually greater, and thus it is effective to use the method of quality determination with the short interval master data in many cases.

According to the second embodiment, the phase difference generated for every observed object or for every region to be observed is cancelled, quality does not rely only on the amplitude intensity, and the automatic determination can be carried out at high accuracy by making a comparison with the acceptable article.

Third Embodiment

A third embodiment of the present invention will now be described. In the third embodiment, a determination method by the conventional gate method will be described using the time phase correction with the long interval master data, which is the first stage described in the second embodiment.

Figure 16:
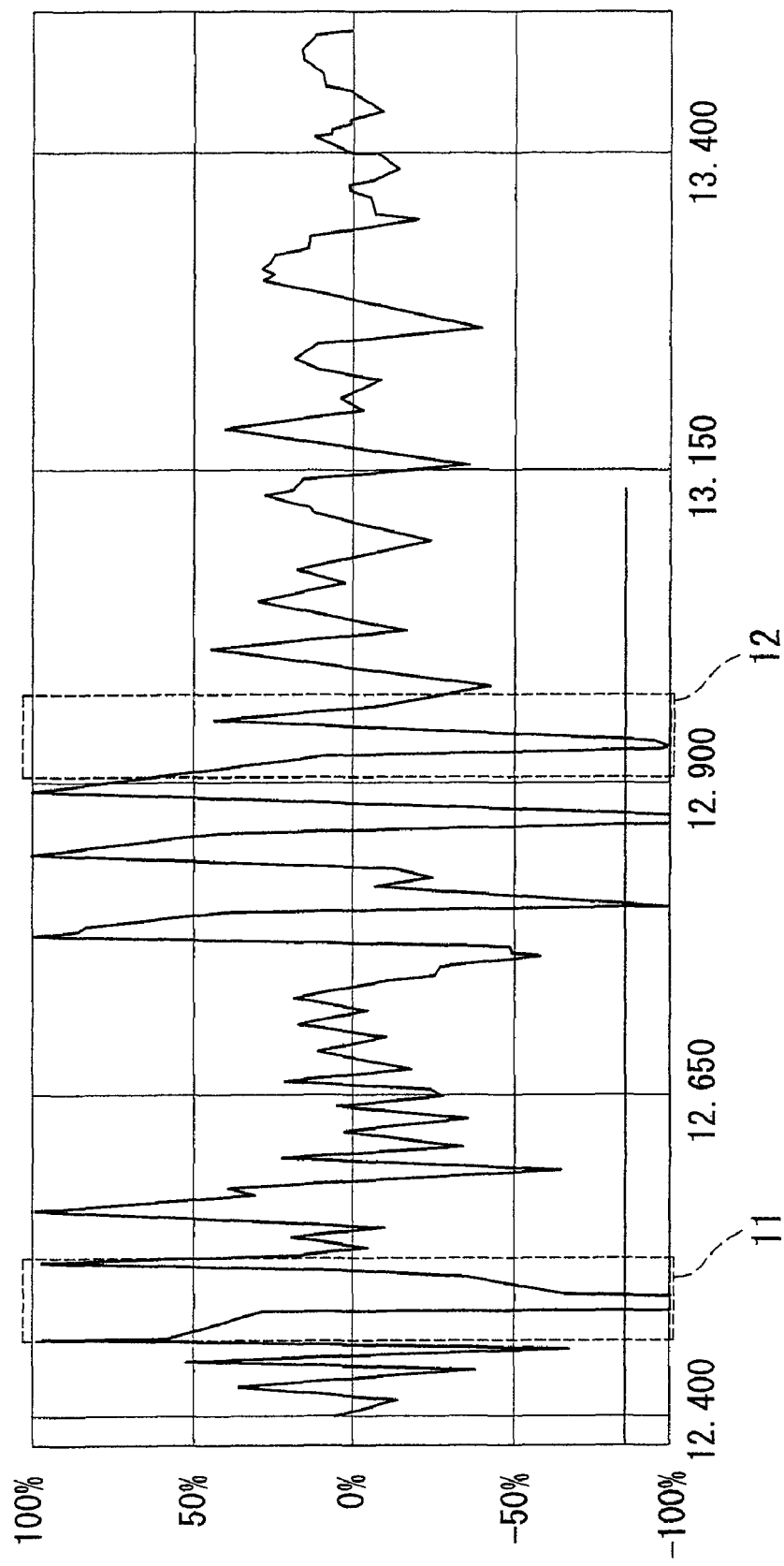
FIG. 16 is a view showing a waveform example of a reflected wave in ultrasonic flaw detection.

As shown in FIG. 16, in the conventional gate method as described in the background art, the trigger 11 is applied to the surface wave, the gate 12 is set to the waveform position to observe with the position applied with the trigger 11 as the zero reference, comparison with the zero reference is carried out by the waveform component in the gate 12, and quality determination of an observed object 102 is performed. That is, the time correction of the waveform is performed by the trigger 11 of the surface wave. However, as described in the "Issues to be solved by the Invention", temporal shift may occur even in the waveform after the trigger 11 by the surface wave as shown in FIG. 19, and the time correction by the surface trigger is not sufficient.

Figure 12:
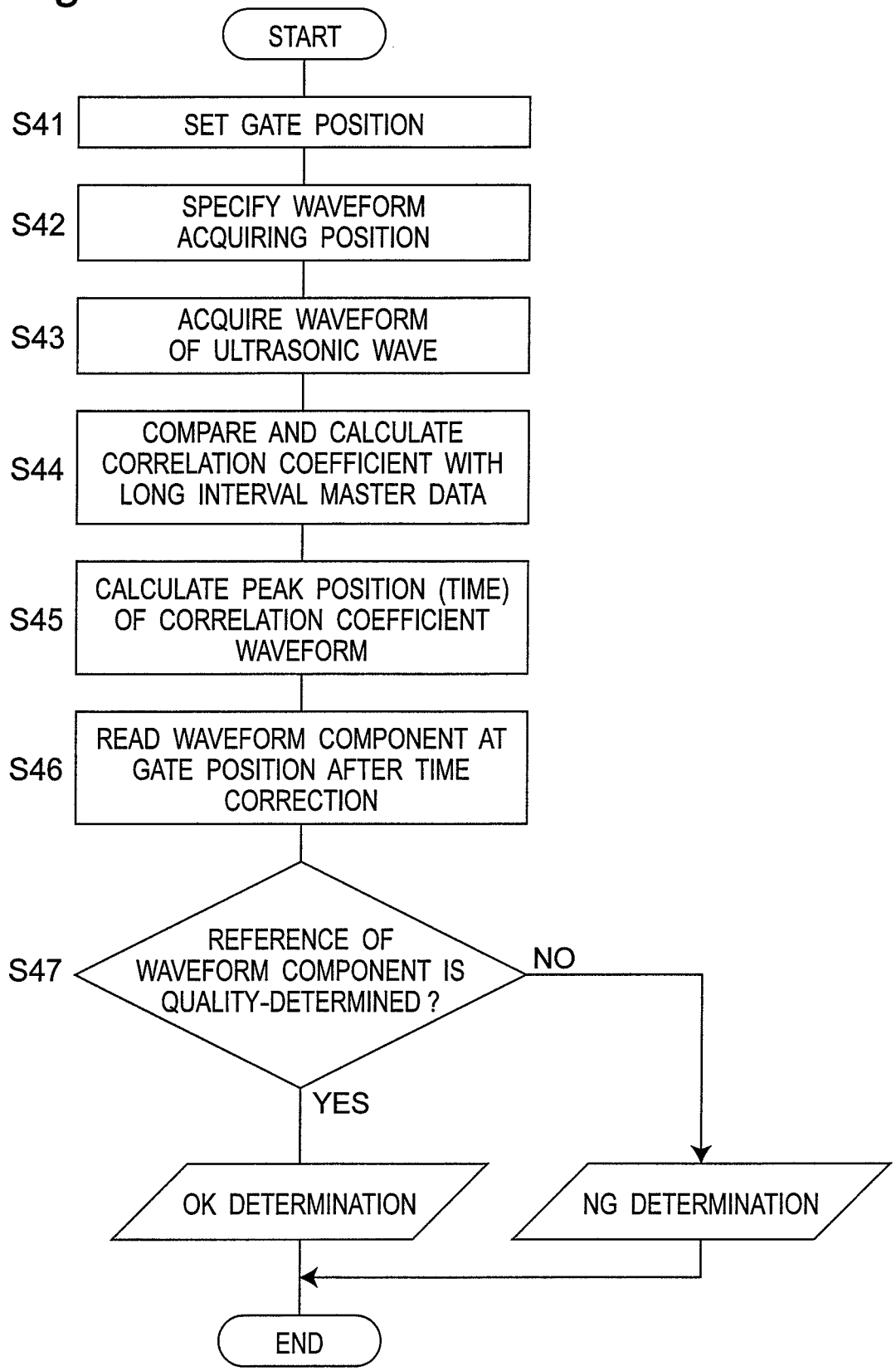
FIG. 12 is a flowchart showing a determination method according to a gate method using a time phase correction by the long interval master data according to a third embodiment.

In order to solve such issues, a method of performing determination by the conventional gate method after carrying out time phase correction by the long interval master data described in the second embodiment is described as the ultrasonic wave measuring method and apparatus according to the third embodiment of the present invention. FIG. 12 shows a flowchart of the determination method by the gate method using the time phase correction by the long interval master data of the third embodiment.

As a rough process, the position of the gate 61 is set in advance in the data calculating unit 34 (step S41), the time phase correction is performed by the data calculating unit 34 with the long interval master data (steps S42 to S45), and quality determination is performed in the determining unit 35 by comparing the waveform components in the gate (steps S46 to S47). Similar to the determination with the long interval master data described above, the BGA chips (first and second samples) 51, 52 of FIG. 3A and FIG. 3B are used as an example of the observed object 2.

Figure 13:
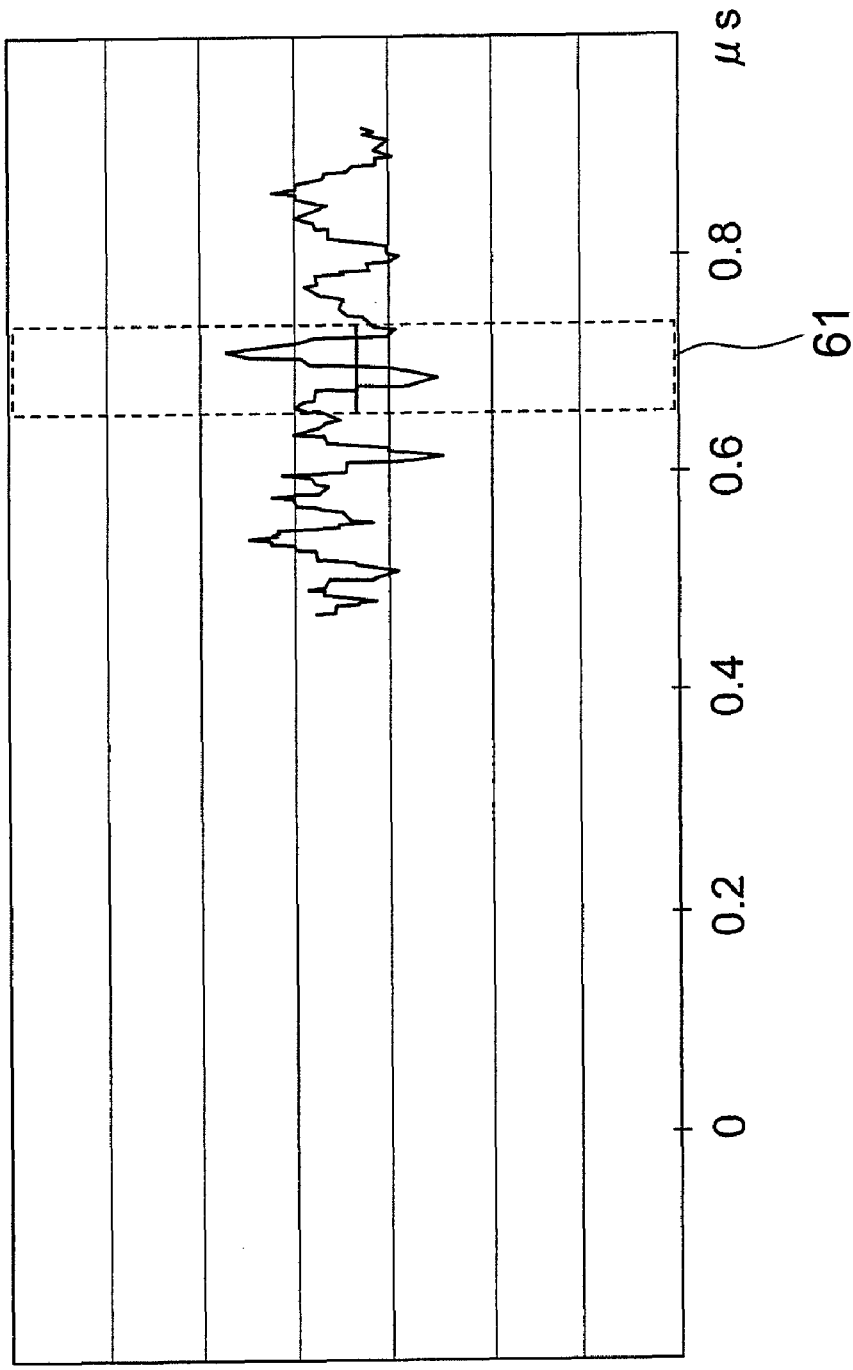
FIG. 13 is a view describing a gate setting method from the master data according to the third embodiment (unit of vertical axis is arbitrary intensity value and the horizontal axis is time (μs))
Figure 15:
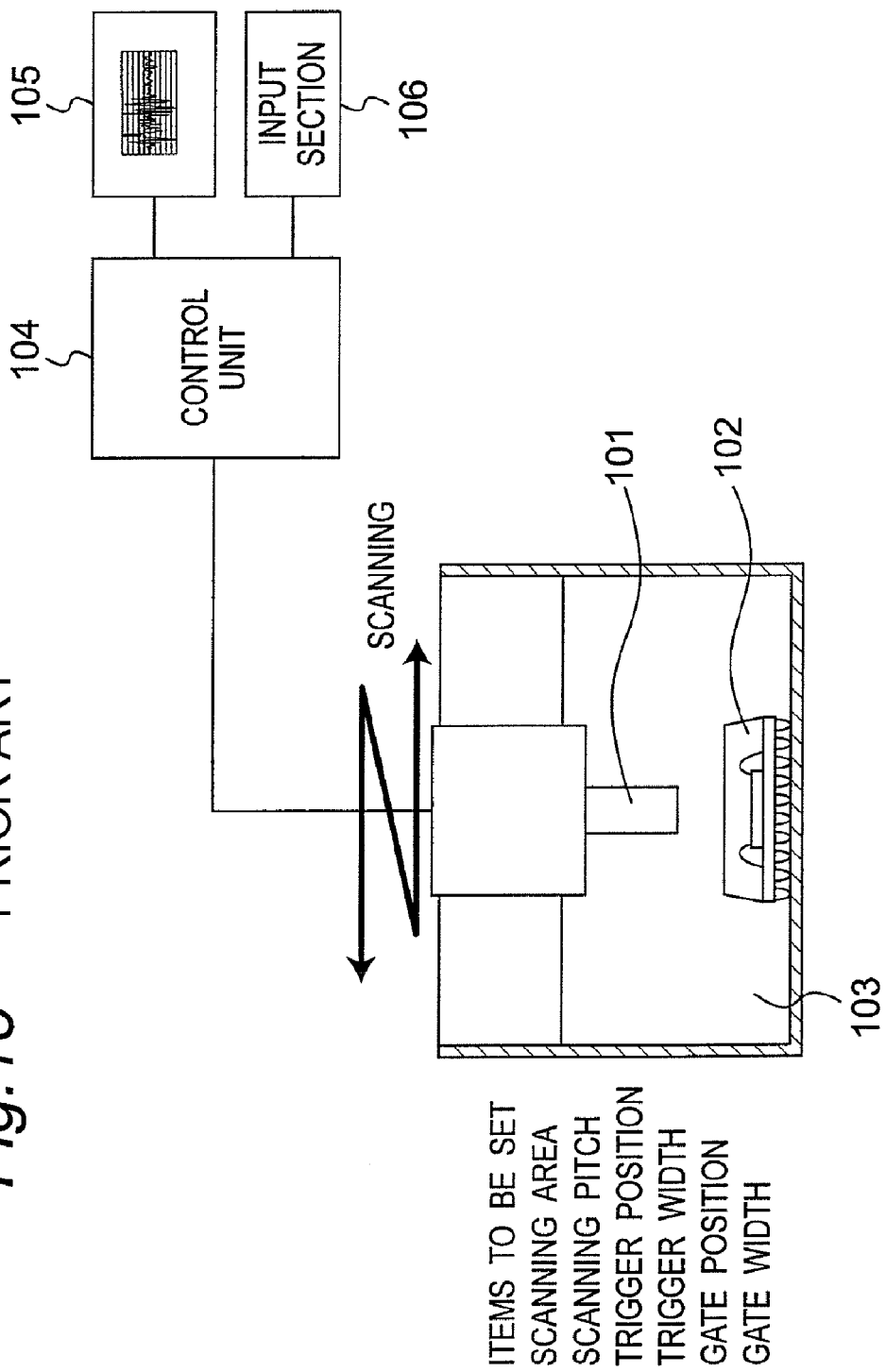
FIG. 15 is a view showing a basic configuration of a conventional ultrasonic wave measuring apparatus.

As a first stage, the gate position of the waveform is set. In the setting of the gate position, the gate position may be set in the data calculating unit 34 from the long interval master data created in advance. FIG. 13 shows an explanatory view of the method of setting the gate 61 from the long interval master data. The gate 61 is set at the time position to observe, in the master data holding memory 36 by the input section 6 from the long interval master data (step S41). The determination is performed in the determining unit 35 with the waveform in the gate position. With the observation spot where the time phase is corrected by the long interval master data being used as the zero reference, the subsequent time or the data region is specified in the master data holding memory 36 by the input section 6 with the gate 61.

The time phase correction by the long interval master data in the second stage is substantially the same process as the determination method with the long interval master data of the first embodiment.

First, the measurement position of the second sample 52 of the observed object 2 is specified in the measurement position data memory 37 with the input section 6 (step S42). The specifying manner is the same as step S11.

The ultrasonic wave is then emitted from the ultrasonic probe 1 towards the measurement position of the second sample 52, the wave reflected from the measurement position of the second sample 52 is received by the ultrasonic probe 1, and the waveform data is acquired by the reception circuit 31, similar to step S12 (step S43).

Next, the comparison calculation of the master data of the first sample 51 stored in the master data holding memory 36 and the waveform data of the second sample 52 inputted and acquired from the A/D circuit 32 is performed by the data calculating unit 34 using correlation coefficient (step S44).

Next, the data position that becomes the spectrum peak (interface to measure) of the correlation coefficient waveform by the long interval master data is acquired in the data calculating unit 34, similar to step S34 (step S45).

The time phase thus can be corrected by samples or by locations, the gate position can be set in the master data holding memory 36 by the input section 6 from the zero reference point of the acquired waveform obtained from the correlation coefficient waveform as described above, and the waveform component is acquired in the data calculating unit 34 (step S46). The waveform component includes the maximum value and the minimum value (negative maximum value) of the waveform intensity in the gate interval, the maximum value of the absolute value, or the like. Such components are acquired in the data calculating unit 34, the waveform components exceeding the determination reference set in advance are determined as OK in the determining unit 35, the waveform components not exceeding the determination reference are determined as NG, and are then outputted to the output section 5 and displayed on the display.

According to the third embodiment, this can be used as the method of performing determination by the conventional gate method after performing the time phase correction according to the previous embodiments. That is, time difference of the waveform exists in the subsequent waveforms even if the trigger is applied to the surface as shown in FIG. 19 in the conventional gate method, but time correction becomes possible according to the third embodiment. Compared to the second embodiment (the short interval master data method), the calculation time for determination can be reduced. That is, in the short interval master data, the calculation of the above calculation formula (equation 2) needs to be performed by the number of segmentations m. In the method of the third embodiment, on the other hand, the intensity information of the amplitude of the gate interval of the master data only needs to be observed after the correction of the long interval master data, and thus the calculation amount can be reduced (quality determination is performed with the intensity information). Furthermore, according to the third embodiment, similar to the other embodiments, the phase difference generated for every observed object or for every region to be observed is cancelled, quality does not rely only on the amplitude intensity, and the automatic determination can be carried out at high accuracy by making a comparison with the acceptable article.

Fourth Embodiment

An ultrasonic wave measuring method and apparatus according to a fourth embodiment of the present invention will now be described. In the second embodiment, an example where the time phase correction using the long interval master data is performed as the first stage, and the determination with the short interval master data is performed as the second stage is shown. However, the determination with the short interval master data of the second stage does not necessarily need to be performed after the time phase correction of the first stage, and only the determination with the short interval master data may be performed. This example will be shown below.

FIG. 14 shows an explanatory view of a determination method with the short interval master data in which the time phase correction is not performed according to the fourth embodiment. Similar to the second embodiment, the long interval master data is created in advance, and the segmentation width of the long interval master data and the like is set. In the example of FIG. 14, the long interval master data is equally divided by ten, but does not necessarily need to be equally divided.

The starting point of the master data is then matched with one of the points of the acquired waveform in the data calculating unit 34. In FIG. 14, the starting point of the master data is matched with the starting point of the acquired waveform in the data calculating unit 34, but does not necessarily need to be matched with the starting point, and may be matched with the middle point of the acquired waveform in the data calculating unit 34.

The acquired waveform is then segmentalized by the data calculating unit 34 with the time width similar to each short interval master data, and the correlation coefficient process is performed in the data calculating unit 34 using the data of each time width and the data of each time width of the short interval master data. If the time width of the master data is 400 ns and the dividing number is ten, the width of each short interval master data becomes 40 ns if the time width 400 ns is equally divided by ten. Here, if the starting point of the master data is matched with the starting point of the acquired waveform by the data calculating unit 34, ten segmentalized data of every 40 ns are set from the starting point in the acquired waveform. Next, the correlation coefficient values of each data of the acquired waveform and each data of the short interval master data are obtained by the data calculating unit 34.

The master data is then shifted in the data calculating unit 34 by a certain set width as in FIG. 14, the acquired waveform is similarly segmentalized in the data calculating unit 34, and the correlation coefficient values are obtained in the data calculating unit 34. As a set value, the time width of the sampling data, the time width of the master data, or the like may be arbitrarily set through the input section 6 in the data calculating unit 34. The interval of the set width does not need to be constant, and the master data does not need to be shifted to the terminating point of the data of the observed waveform.

Therefore, the correlation coefficient value for the dividing number is calculated in the data calculating unit 34 for every starting point of the master data. In this example, ten correlation coefficient values exist with respect to one starting point, where after the shift is repeated twenty times and ten correlation coefficient values are respectively calculated in the data calculating unit 34, a total of two hundred correlation coefficient values are ultimately calculated in the data calculating unit 34.

The method of determining quality in the above-described method includes comprehensively determining the correlation coefficient value of each dividing point, the starting point of the master data, or the like in the determining unit 35, and thus, determining quality in the determining unit 35. For instance, the determination method is adopted where when ten correlation coefficient values are calculated in the data calculating unit 34 with respect to a certain starting point, determination is made as acceptable article in the determining unit 35 if seven of the ten correlation coefficient values exceed a certain constant value (threshold value) (e.g., greater than or equal to 0.8) at all the starting points. Alternatively, if seven of the ten correlation coefficient values exceed the certain constant value (threshold value), assuming the starting point contains the information of the interface to observe (i.e., assumed that correlation exists with the master data), the determination method of determining the correlation coefficient values at the observation spots of a certain time width (e.g., third, eighth of the ten segmentation points) in the determining unit 35, and thus, performing quality determination may be adopted.

Regarding the determination method, determination may be made in view of various factors such as the type, length, or number of segmentations of the cutout master data.

In the master data, the data is acquired by measuring the acceptable article, but the master data may be acquired from the design data through calculation.

The present invention is not limited to the embodiments described above, and various modifications can be made without departing from the scope of the idea of the present invention.

By properly combining the arbitrary embodiments of the aforementioned various embodiments, the effects possessed by the embodiments can be produced.

INDUSTRIAL APPLICABILITY

The ultrasonic wave measuring method and the apparatus according to the present invention perform ultrasonic wave measurement by canceling the phase difference created for every observed object (detected object) or every region to be observed, comparing the ultrasonic wave waveform signal acquired from the detected object and the reference signal, and thus obtaining a relative value. The present invention is useful as measurement method and apparatus capable of performing comparison with the acceptable article by using the acquired relative value without depending only on the amplitude intensity, performing automatic determination at high accuracy, and detecting and analyzing a defect such as joint separation or a crack at high accuracy with respect to the observed object having a microscopic thickness and interfaces of multi-layers.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

The invention claimed is:

1. An ultrasonic wave measuring method of irradiating with an ultrasonic wave an object to be detected having a plurality of interfaces, detecting a waveform signal generated from the object, and observing a joint state of a boundary face of the object, the ultrasonic wave measuring method comprising:
saving, for every observation spot of a reference object which cross-sectional structure, material, and thickness are the same as the object in a certain specific region within an XY plane orthogonal to a direction of irradiating with the ultrasonic wave, an entire waveform signal of the reference object or a waveform signal observed from near an interface part of the reference object as a reference signal in a reference signal storage section;
acquiring in a calculating unit an ultrasonic wave waveform signal acquired at an observation spot of the object corresponding to the observation spot of the reference object and near the interface part to be observed in which a generating time region is limited from a thickness known in advance and a sonic speed of the ultrasonic wave; and
comparing and calculating the ultrasonic wave waveform signal acquired from the object and the reference signal to obtain a relative value, and observing the joint state of the boundary face in the calculating unit,
wherein in the observing of the joint state of the boundary face, the object having the plurality of interfaces is irradiated with the ultrasonic wave, the comparing and calculating is performed in the calculating unit between the waveform signal observed from the object and the reference signal, a time phase difference generated for every observed waveform signal is corrected in the calculating unit by having a point where the two waveform signals best match as a reference point, and thereafter quality determination is performed in a determining section by comparing waveform components within a predetermined time region in the XY plane specified in advance.

2. The ultrasonic wave measuring method according to claim 1, wherein the object having the plurality of interfaces is irradiated with the ultrasonic wave, the comparing and calculating is performed in the calculating unit between a short interval region waveform signal and a short interval region reference signal, obtained by dividing the waveform signal observed from the object and the reference signal respectively into a plurality of regions in a time direction, and values of calculation results in the respective regions are compared in a determining section.

3. An ultrasonic wave measuring apparatus for irradiating with an ultrasonic wave an object to be detected having a plurality of interfaces, detecting a waveform signal generated from the object, and observing a joint state of a boundary face of the object, the ultrasonic wave measuring apparatus comprising:

an ultrasonic wave transmission and reception device for irradiating with the ultrasonic wave the object and detecting the waveform signal generated from the object;

a reference signal storage section for saving, for every observation spot of a reference object which cross-sectional structure, material, and thickness are the same as the object in a certain specific region within an XY plane orthogonal to a direction of irradiating with the ultrasonic wave, an entire waveform signal of the reference object or a waveform signal observed from near an interface part of the reference object, as a reference signal; and a calculating unit for acquiring an ultrasonic wave waveform signal acquired at an observation spot of the object corresponding to the observation spot of the reference object and near the interface part to be observed in which a generating time region is limited from a thickness known in advance and a sonic speed of the ultrasonic wave, and comparing and calculating the ultrasonic wave waveform signal acquired from the object and the reference signal to obtain a relative value, and thus, observing the joint state of the boundary face, wherein the object having the plurality of interfaces is irradiated with the ultrasonic wave, the calculating unit performs calculating and comparing between the waveform signal acquired from the object and the reference signal, the ultrasonic wave measuring apparatus further comprising a determining section that performs quality determination by comparing waveform components within a predetermined time region in the XY plane specified in advance after the calculating unit corrects a time phase difference generated for every observed waveform signal by having a point where the two waveform signals best match as a reference point.

* * * * *